(12) United States Patent
Schoenefeld et al.

(10) Patent No.: US 8,282,646 B2
(45) Date of Patent: Oct. 9, 2012

(54) PATIENT SPECIFIC KNEE ALIGNMENT GUIDE AND ASSOCIATED METHOD

(75) Inventors: Ryan J. Schoenefeld, Fort Wayne, IN (US); Scott Deming, Warsaw, IN (US); Garrett A. Sheffer, Warsaw, IN (US); Robert Metzger, Wakarusa, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 1074 days.

(21) Appl. No.: 12/039,849

(22) Filed: Feb. 29, 2008

(65) Prior Publication Data

US 2008/0161815 A1 Jul. 3, 2008

Related U.S. Application Data

(63) Continuation-in-part of application No. 11/756,057, filed on May 31, 2007, now Pat. No. 8,092,465, which is a continuation-in-part of application No. 11/971,390, filed on Jan. 9, 2008, now Pat. No. 8,070,752, which is a continuation-in-part of application No. 11/363,548, filed on Feb. 27, 2006, now Pat. No. 7,780,672, which is a continuation-in-part of application No. 12/025,414, filed on Feb. 4, 2008.

(60) Provisional application No. 60/812,694, filed on Jun. 9, 2006, provisional application No. 60/953,637, filed on Aug. 2, 2007, provisional application No. 60/953,620, filed on Aug. 2, 2007, provisional application No. 60/947,813, filed on Jul. 3, 2007, provisional application No. 60/911,297, filed on Apr. 12, 2007, provisional application No. 60/892,349, filed on Mar. 1, 2007.

(51) Int. Cl.
*A61B 17/58* (2006.01)
(52) U.S. Cl. .......................................................... 606/88
(58) Field of Classification Search ................ 606/86 R, 606/87–89, 104; 623/20.14–20.36
See application file for complete search history.

(56) References Cited

U.S. PATENT DOCUMENTS 1,480,285 A 1/1924 Moore
(Continued)

FOREIGN PATENT DOCUMENTS

CA 2447694 A1 12/2002
(Continued)

OTHER PUBLICATIONS

Great Britain Search Report mailed Dec. 21, 2011 for GB1116054.6, claiming benefit of U.S. Appl. No. 12/888,005, filed Sep. 22, 2010.

(Continued)

*Primary Examiner* — Kevin T Truong
*Assistant Examiner* — Christopher Beccia
(74) *Attorney, Agent, or Firm* — Harness, Dickey

(57) ABSTRACT

An orthopedic apparatus including a patient-specific alignment guide attachable to a surface of a bone being prepared for receiving a prosthetic implant. The guide includes at least first and second components and a coupling mechanism connecting the first and second components to one another. The first component has a first bone engagement surface and the second component has a second bone engagement surface, the first and second bone engagement surfaces anatomically matching corresponding first and second portions of the surface of the bone. At least one of the first and second components defines at least one alignment formation.

13 Claims, 22 Drawing Sheets

U.S. PATENT DOCUMENTS

| | | |
|---|---|---|
| 2,181,746 A | 11/1939 | Siebrandt |
| 2,407,845 A | 9/1946 | Nemeyer |
| 2,618,913 A | 11/1952 | Plancon et al. |
| 2,910,978 A | 11/1959 | Urist |
| 3,840,904 A | 10/1974 | Tronzo |
| 4,246,895 A | 1/1981 | Rehder |
| 4,306,866 A | 12/1981 | Weissman |
| 4,324,006 A | 4/1982 | Charnley |
| 4,436,684 A | 3/1984 | White |
| 4,475,549 A | 10/1984 | Oh |
| 4,506,393 A | 3/1985 | Murphy |
| 4,524,766 A | 6/1985 | Petersen |
| 4,619,658 A | 10/1986 | Pappas et al. |
| 4,621,630 A | 11/1986 | Kenna |
| 4,632,111 A | 12/1986 | Roche |
| 4,633,862 A | 1/1987 | Petersen |
| 4,663,720 A | 5/1987 | Duret et al. |
| 4,695,283 A | 9/1987 | Aldinger |
| 4,696,292 A | 9/1987 | Heiple |
| 4,703,751 A | 11/1987 | Pohl |
| 4,704,686 A | 11/1987 | Aldinger |
| 4,721,104 A | 1/1988 | Kaufman et al. |
| 4,778,474 A | 10/1988 | Homsy |
| 4,800,874 A | 1/1989 | David et al. |
| 4,821,213 A | 4/1989 | Cline et al. |
| 4,822,365 A | 4/1989 | Walker et al. |
| 4,841,975 A | 6/1989 | Woolson |
| 4,846,161 A | 7/1989 | Roger |
| 4,871,975 A | 10/1989 | Nawata et al. |
| 4,893,619 A | 1/1990 | Dale et al. |
| 4,896,663 A | 1/1990 | Vandewalls |
| 4,927,422 A | 5/1990 | Engelhardt |
| 4,936,862 A | 6/1990 | Walker et al. |
| 4,959,066 A | 9/1990 | Dunn et al. |
| 4,976,737 A | 12/1990 | Leake |
| 4,979,949 A | 12/1990 | Matsen, III et al. |
| 4,985,037 A | 1/1991 | Petersen |
| 5,002,579 A | 3/1991 | Copf et al. |
| 5,007,936 A | 4/1991 | Woolson |
| 5,030,221 A | 7/1991 | Buechel et al. |
| 5,041,117 A | 8/1991 | Engelhardt |
| 5,053,039 A | 10/1991 | Hofmann et al. |
| 5,086,401 A | 2/1992 | Glassman et al. |
| 5,098,383 A | 3/1992 | Hemmy et al. |
| 5,098,436 A | 3/1992 | Ferrante et al. |
| 5,108,425 A | 4/1992 | Hwang |
| 5,122,144 A | 6/1992 | Bert et al. |
| 5,129,908 A | 7/1992 | Petersen |
| 5,129,909 A | 7/1992 | Sutherland |
| 5,133,760 A | 7/1992 | Petersen et al. |
| 5,140,777 A | 8/1992 | Ushiyama et al. |
| 5,150,304 A | 9/1992 | Berchem et al. |
| 5,176,684 A | 1/1993 | Ferrante et al. |
| 5,258,032 A | 11/1993 | Bertin |
| 5,261,915 A | 11/1993 | Durlacher et al. |
| 5,274,565 A | 12/1993 | Reuben |
| 5,299,288 A | 3/1994 | Glassman et al. |
| 5,300,077 A | 4/1994 | Howell |
| 5,320,625 A | 6/1994 | Bertin |
| 5,342,366 A | 8/1994 | Whiteside et al. |
| 5,344,423 A | 9/1994 | Dietz et al. |
| 5,360,446 A | 11/1994 | Kennedy |
| 5,368,858 A | 11/1994 | Hunziker |
| 5,370,692 A | 12/1994 | Fink et al. |
| 5,370,699 A | 12/1994 | Hood et al. |
| 5,405,395 A | 4/1995 | Coates |
| 5,408,409 A | 4/1995 | Glassman et al. |
| 5,415,662 A | 5/1995 | Ferrante et al. |
| 5,438,263 A | 8/1995 | Dworkin et al. |
| 5,440,496 A | 8/1995 | Andersson et al. |
| 5,448,489 A | 9/1995 | Reuben |
| 5,452,407 A | 9/1995 | Crook |
| 5,454,816 A | 10/1995 | Ashby |
| 5,472,415 A | 12/1995 | King et al. |
| 5,474,559 A | 12/1995 | Bertin et al. |
| 5,490,854 A | 2/1996 | Fisher et al. |
| 5,496,324 A | 3/1996 | Barnes |
| 5,507,833 A | 4/1996 | Bohn |
| 5,514,519 A | 5/1996 | Neckers |
| 5,520,695 A | 5/1996 | Luckman |
| 5,527,317 A | 6/1996 | Ashby et al. |
| 5,539,649 A | 7/1996 | Walsh et al. |
| 5,549,688 A | 8/1996 | Ries et al. |
| 5,554,190 A | 9/1996 | Draenert |
| 5,560,096 A | 10/1996 | Stephens |
| 5,571,110 A | 11/1996 | Matsen, III et al. |
| 5,578,037 A | 11/1996 | Sanders et al. |
| 5,595,703 A | 1/1997 | Swaelens et al. |
| 5,607,431 A | 3/1997 | Dudasik et al. |
| 5,620,448 A | 4/1997 | Puddu |
| 5,634,927 A | 6/1997 | Houston et al. |
| 5,658,294 A | 8/1997 | Sederholm |
| 5,662,656 A | 9/1997 | White |
| 5,677,107 A | 10/1997 | Neckers |
| 5,681,354 A | 10/1997 | Eckhoff |
| 5,682,886 A | 11/1997 | Delp et al. |
| 5,690,635 A | 11/1997 | Matsen, III et al. |
| 5,702,460 A | 12/1997 | Carls et al. |
| 5,704,941 A | 1/1998 | Jacober et al. |
| 5,722,978 A | 3/1998 | Jenkins, Jr. |
| 5,725,376 A | 3/1998 | Poirier |
| 5,725,593 A | 3/1998 | Caracciolo |
| 5,735,277 A | 4/1998 | Schuster |
| 5,748,767 A | 5/1998 | Raab |
| 5,749,875 A | 5/1998 | Puddu |
| 5,749,876 A | 5/1998 | Duvillier et al. |
| 5,762,125 A | 6/1998 | Mastrorio |
| 5,768,134 A | 6/1998 | Swaelens et al. |
| 5,769,092 A | 6/1998 | Williamson, Jr. |
| 5,786,217 A | 7/1998 | Tubo et al. |
| 5,792,143 A | 8/1998 | Samuelson et al. |
| 5,798,924 A | 8/1998 | Eufinger et al. |
| 5,799,055 A | 8/1998 | Peshkin et al. |
| 5,860,981 A | 1/1999 | Bertin et al. |
| 5,871,018 A | 2/1999 | Delp et al. |
| 5,876,456 A | 3/1999 | Sederholm et al. |
| 5,879,398 A | 3/1999 | Swarts et al. |
| 5,879,402 A | 3/1999 | Lawes et al. |
| 5,880,976 A | 3/1999 | DiGioia, III et al. |
| 5,885,297 A | 3/1999 | Matsen, III |
| 5,885,298 A | 3/1999 | Herrington et al. |
| 5,895,389 A | 4/1999 | Schenk et al. |
| 5,899,907 A | 5/1999 | Johnson |
| 5,901,060 A | 5/1999 | Schall et al. |
| 5,911,724 A | 6/1999 | Wehrli |
| 5,925,049 A | 7/1999 | Gustilo et al. |
| 5,942,370 A | 8/1999 | Neckers |
| 5,967,777 A | 10/1999 | Klein et al. |
| 5,976,149 A | 11/1999 | Masini |
| 6,033,415 A | 3/2000 | Mittelstadt et al. |
| 6,059,833 A | 5/2000 | Doets |
| 6,086,593 A | 7/2000 | Bonutti |
| 6,120,510 A | 9/2000 | Albrektsson et al. |
| 6,120,544 A | 9/2000 | Grundei et al. |
| 6,126,690 A | 10/2000 | Ateshian et al. |
| 6,136,033 A | 10/2000 | Suemer |
| 6,156,069 A | 12/2000 | Amstutz |
| 6,161,080 A | 12/2000 | Aouni-Ateshian et al. |
| 6,187,010 B1 | 2/2001 | Masini |
| 6,195,615 B1 | 2/2001 | Lysen |
| 6,203,546 B1 | 3/2001 | MacMahon |
| 6,205,411 B1 | 3/2001 | DiGioia, III et al. |
| 6,206,927 B1 | 3/2001 | Fell et al. |
| 6,254,604 B1 | 7/2001 | Howell |
| 6,258,097 B1 | 7/2001 | Cook et al. |
| 6,264,698 B1 | 7/2001 | Lawes et al. |
| 6,273,891 B1 | 8/2001 | Masini |
| 6,290,727 B1 | 9/2001 | Otto et al. |
| 6,293,971 B1 | 9/2001 | Nelson et al. |
| 6,312,473 B1 | 11/2001 | Oshida |
| 6,319,285 B1 | 11/2001 | Chamier et al. |
| 6,325,829 B1 | 12/2001 | Schmotzer |
| 6,343,987 B2 | 2/2002 | Hayama et al. |
| 6,354,011 B1 | 3/2002 | Albrecht |
| 6,379,299 B1 | 4/2002 | Borodulin et al. |
| 6,383,228 B1 | 5/2002 | Schmotzer |
| 6,391,251 B1 | 5/2002 | Keicher et al. |

| | | |
|---|---|---|
| 6,395,005 B1 | 5/2002 | Lovell |
| 6,427,698 B1 | 8/2002 | Yoon |
| 6,459,948 B1 | 10/2002 | Ateshian et al. |
| 6,463,351 B1 | 10/2002 | Clynch |
| 6,475,243 B1 | 11/2002 | Sheldon et al. |
| 6,488,715 B1 | 12/2002 | Pope et al. |
| 6,503,255 B1 | 1/2003 | Albrektsson et al. |
| 6,510,334 B1 | 1/2003 | Schuster et al. |
| 6,514,259 B2 | 2/2003 | Picard et al. |
| 6,517,583 B1 | 2/2003 | Pope et al. |
| 6,520,964 B2 | 2/2003 | Tallarida et al. |
| 6,533,737 B1 | 3/2003 | Brosseau et al. |
| 6,554,837 B1 | 4/2003 | Hauri et al. |
| 6,556,008 B2 | 4/2003 | Thesen |
| 6,558,391 B2 | 5/2003 | Axelson, Jr. et al. |
| 6,558,428 B2 | 5/2003 | Park |
| 6,564,085 B2 | 5/2003 | Meaney et al. |
| 6,567,681 B1 | 5/2003 | Lindequist |
| 6,575,980 B1 | 6/2003 | Robie et al. |
| 6,575,982 B1 | 6/2003 | Bonutti |
| 6,591,581 B2 | 7/2003 | Schmieding |
| 6,605,293 B1 | 8/2003 | Giordano et al. |
| 6,622,567 B1 | 9/2003 | Hamel et al. |
| 6,629,999 B1 | 10/2003 | Serafin, Jr. |
| 6,641,617 B1 | 11/2003 | Merrill et al. |
| 6,682,566 B2 | 1/2004 | Draenert |
| 6,696,073 B2 | 2/2004 | Boyce et al. |
| 6,697,664 B2 | 2/2004 | Kienzle, III et al. |
| 6,701,174 B1 | 3/2004 | Krause et al. |
| 6,709,462 B2 | 3/2004 | Hanssen |
| 6,711,431 B2 | 3/2004 | Sarin et al. |
| 6,711,432 B1 | 3/2004 | Krause et al. |
| 6,712,856 B1 | 3/2004 | Carignan et al. |
| 6,716,249 B2 | 4/2004 | Hyde |
| 6,725,077 B1 | 4/2004 | Balloni et al. |
| 6,738,657 B1 | 5/2004 | Franklin et al. |
| 6,740,092 B2 | 5/2004 | Lombardo et al. |
| 6,749,638 B1 | 6/2004 | Saladino |
| 6,750,653 B1 | 6/2004 | Zou et al. |
| 6,772,026 B2 | 8/2004 | Bradbury et al. |
| 6,780,190 B2 | 8/2004 | Maroney |
| 6,786,930 B2 | 9/2004 | Biscup |
| 6,799,066 B2 | 9/2004 | Steines et al. |
| 6,823,871 B2 | 11/2004 | Schmieding |
| 6,827,723 B2 | 12/2004 | Carson |
| 6,887,247 B1 | 5/2005 | Couture et al. |
| 6,905,514 B2 | 6/2005 | Carignan et al. |
| 6,923,817 B2 | 8/2005 | Carson et al. |
| 6,923,831 B2 | 8/2005 | Fell et al. |
| 6,932,842 B1 | 8/2005 | Litschko et al. |
| 6,942,475 B2 | 9/2005 | Ensign et al. |
| 6,944,518 B2 | 9/2005 | Roose |
| 6,945,976 B2 | 9/2005 | Ball et al. |
| 6,953,480 B2 | 10/2005 | Mears et al. |
| 6,960,216 B2 | 11/2005 | Kolb et al. |
| 6,990,220 B2 | 1/2006 | Ellis et al. |
| 7,029,479 B2 | 4/2006 | Tallarida et al. |
| 7,042,222 B2 | 5/2006 | Zheng et al. |
| 7,048,741 B2 | 5/2006 | Swanson |
| 7,050,877 B2 | 5/2006 | Iseki et al. |
| 7,060,074 B2 | 6/2006 | Rosa et al. |
| 7,074,241 B2 | 7/2006 | McKinnon |
| RE39,301 E | 9/2006 | Bertin |
| 7,104,997 B2 | 9/2006 | Lionberger et al. |
| 7,105,026 B2 | 9/2006 | Johnson et al. |
| 7,115,131 B2 | 10/2006 | Engh et al. |
| 7,141,053 B2 | 11/2006 | Rosa et al. |
| 7,169,185 B2 | 1/2007 | Sidebotham |
| 7,176,466 B2 | 2/2007 | Rousso et al. |
| 7,184,814 B2 | 2/2007 | Lang et al. |
| 7,198,628 B2 | 4/2007 | Ondrla et al. |
| 7,218,232 B2 | 5/2007 | DiSilvestro et al. |
| 7,239,908 B1 | 7/2007 | Alexander et al. |
| 7,241,315 B2 | 7/2007 | Evans |
| 7,255,702 B2 | 8/2007 | Serra et al. |
| 7,258,701 B2 | 8/2007 | Aram et al. |
| 7,275,218 B2 | 9/2007 | Petrella et al. |
| 7,282,054 B2 | 10/2007 | Steffensmeier et al. |
| 7,294,133 B2 | 11/2007 | Zink et al. |
| 7,297,164 B2 | 11/2007 | Johnson et al. |
| 7,309,339 B2 | 12/2007 | Cusick et al. |
| 7,333,013 B2 | 2/2008 | Berger |
| 7,335,231 B2 | 2/2008 | McLean |
| 7,371,260 B2 | 5/2008 | Malinin |
| 7,383,164 B2 | 6/2008 | Aram et al. |
| 7,385,498 B2 | 6/2008 | Dobosz |
| 7,388,972 B2 | 6/2008 | Kitson |
| 7,392,076 B2 | 6/2008 | Moctezuma de La Barrera |
| 7,427,200 B2 | 9/2008 | Noble et al. |
| 7,427,272 B2 | 9/2008 | Richard et al. |
| 7,468,075 B2 | 12/2008 | Lang et al. |
| 7,474,223 B2 | 1/2009 | Nycz et al. |
| 7,488,325 B2 | 2/2009 | Qian |
| 7,527,631 B2 | 5/2009 | Maroney et al. |
| 7,534,263 B2 | 5/2009 | Burdulis, Jr. et al. |
| 7,542,791 B2 | 6/2009 | Mire et al. |
| 7,559,931 B2 | 7/2009 | Stone |
| 7,575,602 B2 | 8/2009 | Amirouche et al. |
| 7,578,851 B2 | 8/2009 | Dong et al. |
| 7,582,091 B2 | 9/2009 | Duncan et al. |
| 7,591,821 B2 | 9/2009 | Kelman |
| 7,601,155 B2 | 10/2009 | Petersen |
| 7,604,639 B2 | 10/2009 | Swanson |
| 7,611,516 B2 | 11/2009 | Maroney |
| 7,618,451 B2 | 11/2009 | Berez et al. |
| 7,621,915 B2 | 11/2009 | Frederick et al. |
| 7,625,409 B2 | 12/2009 | Saltzman et al. |
| 7,646,161 B2 | 1/2010 | Albu-Schaffer et al. |
| 7,651,501 B2 | 1/2010 | Penenberg et al. |
| 7,670,345 B2 | 3/2010 | Plassky et al. |
| 7,682,398 B2 | 3/2010 | Croxton et al. |
| 7,695,477 B2 | 4/2010 | Creger et al. |
| 7,695,521 B2 | 4/2010 | Ely et al. |
| 7,699,847 B2 | 4/2010 | Sheldon et al. |
| 7,704,253 B2 | 4/2010 | Bastian et al. |
| 7,794,466 B2 | 9/2010 | Merchant et al. |
| 7,794,467 B2 * | 9/2010 | McGinley et al. ............... 606/88 |
| 7,794,504 B2 | 9/2010 | Case |
| 7,806,896 B1 | 10/2010 | Bonutti |
| 7,809,184 B2 | 10/2010 | Neubauer et al. |
| 7,819,925 B2 | 10/2010 | King et al. |
| 7,828,806 B2 | 11/2010 | Graf et al. |
| 7,879,109 B2 | 2/2011 | Borden et al. |
| 7,892,261 B2 | 2/2011 | Bonutti |
| 7,896,921 B2 | 3/2011 | Smith et al. |
| 7,935,119 B2 | 5/2011 | Ammann et al. |
| 7,938,861 B2 | 5/2011 | King et al. |
| 7,962,196 B2 | 6/2011 | Tuma |
| 7,963,968 B2 | 6/2011 | Dees, Jr. |
| 7,967,823 B2 | 6/2011 | Ammann et al. |
| 7,974,677 B2 | 7/2011 | Mire et al. |
| 7,981,158 B2 | 7/2011 | Fitz et al. |
| 7,993,353 B2 | 8/2011 | Rossner et al. |
| 8,062,301 B2 | 11/2011 | Ammann et al. |
| 8,083,746 B2 | 12/2011 | Novak |
| 8,133,230 B2 | 3/2012 | Stevens et al. |
| 8,137,406 B2 | 3/2012 | Novak et al. |
| 2001/0005797 A1 | 6/2001 | Barlow et al. |
| 2001/0011190 A1 | 8/2001 | Park |
| 2001/0054478 A1 | 12/2001 | Watanabe et al. |
| 2002/0007294 A1 | 1/2002 | Bradbury et al. |
| 2002/0059049 A1 | 5/2002 | Bradbury et al. |
| 2002/0082741 A1 | 6/2002 | Mazumder et al. |
| 2002/0087274 A1 | 7/2002 | Alexander et al. |
| 2002/0107522 A1 * | 8/2002 | Picard et al. .................... 606/88 |
| 2002/0128872 A1 | 9/2002 | Giammattei |
| 2002/0147415 A1 | 10/2002 | Martelli |
| 2003/0009171 A1 | 1/2003 | Tornier |
| 2003/0009234 A1 | 1/2003 | Treacy et al. |
| 2003/0011624 A1 | 1/2003 | Ellis |
| 2003/0018338 A1 | 1/2003 | Axelson et al. |
| 2003/0039676 A1 | 2/2003 | Boyce et al. |
| 2003/0055502 A1 | 3/2003 | Lang et al. |
| 2003/0109784 A1 | 6/2003 | Loh et al. |
| 2003/0120276 A1 | 6/2003 | Tallarida et al. |
| 2003/0139817 A1 | 7/2003 | Tuke et al. |
| 2003/0158606 A1 | 8/2003 | Coon et al. |
| 2003/0171757 A1 | 9/2003 | Coon et al. |

| | | |
|---|---|---|
| 2003/0216669 A1 | 11/2003 | Lang et al. |
| 2004/0018144 A1 | 1/2004 | Briscoe |
| 2004/0030245 A1 | 2/2004 | Noble et al. |
| 2004/0054372 A1 | 3/2004 | Corden et al. |
| 2004/0068187 A1 | 4/2004 | Krause et al. |
| 2004/0092932 A1 | 5/2004 | Aubin et al. |
| 2004/0098133 A1 | 5/2004 | Carignan et al. |
| 2004/0102852 A1 | 5/2004 | Johnson et al. |
| 2004/0102866 A1 | 5/2004 | Harris et al. |
| 2004/0106926 A1 | 6/2004 | Leitner et al. |
| 2004/0115586 A1 | 6/2004 | Andreiko et al. |
| 2004/0122439 A1 | 6/2004 | Dwyer et al. |
| 2004/0128026 A1 | 7/2004 | Harris et al. |
| 2004/0133276 A1 | 7/2004 | Lang et al. |
| 2004/0138754 A1 | 7/2004 | Lang et al. |
| 2004/0143336 A1 | 7/2004 | Burkinshaw |
| 2004/0147927 A1 | 7/2004 | Tsougarakis et al. |
| 2004/0153079 A1 | 8/2004 | Tsougarakis et al. |
| 2004/0153087 A1 | 8/2004 | Sanford et al. |
| 2004/0158254 A1 | 8/2004 | Eisermann |
| 2004/0162619 A1 | 8/2004 | Blaylock et al. |
| 2004/0167390 A1 | 8/2004 | Alexander et al. |
| 2004/0171924 A1 | 9/2004 | Mire et al. |
| 2004/0172137 A1 | 9/2004 | Blaylock et al. |
| 2004/0181144 A1 | 9/2004 | Cinquin et al. |
| 2004/0204644 A1 | 10/2004 | Tsougarakis et al. |
| 2004/0204760 A1 | 10/2004 | Fitz et al. |
| 2004/0212586 A1 | 10/2004 | Denny |
| 2004/0220583 A1* | 11/2004 | Pieczynski et al. ............ 606/102 |
| 2004/0236341 A1 | 11/2004 | Petersen |
| 2004/0236424 A1 | 11/2004 | Berez et al. |
| 2004/0243481 A1 | 12/2004 | Bradbury et al. |
| 2004/0254584 A1 | 12/2004 | Sarin et al. |
| 2004/0260301 A1 | 12/2004 | Lionberger et al. |
| 2005/0008887 A1 | 1/2005 | Haymann et al. |
| 2005/0010300 A1 | 1/2005 | Disilvestro et al. |
| 2005/0015022 A1 | 1/2005 | Richard et al. |
| 2005/0019664 A1 | 1/2005 | Matsumoto |
| 2005/0027303 A1 | 2/2005 | Lionberger et al. |
| 2005/0027361 A1 | 2/2005 | Reiley |
| 2005/0043806 A1 | 2/2005 | Cook et al. |
| 2005/0043837 A1 | 2/2005 | Rubbert et al. |
| 2005/0049524 A1 | 3/2005 | Lefevre et al. |
| 2005/0049603 A1* | 3/2005 | Calton et al. .................... 606/87 |
| 2005/0059873 A1 | 3/2005 | Glozman et al. |
| 2005/0060040 A1 | 3/2005 | Auxepaules et al. |
| 2005/0065628 A1 | 3/2005 | Roose |
| 2005/0070897 A1 | 3/2005 | Petersen |
| 2005/0071015 A1 | 3/2005 | Sekel |
| 2005/0075641 A1 | 4/2005 | Singhatat et al. |
| 2005/0096535 A1 | 5/2005 | de la Barrera |
| 2005/0113841 A1 | 5/2005 | Sheldon et al. |
| 2005/0113846 A1 | 5/2005 | Carson |
| 2005/0119664 A1 | 6/2005 | Carignan et al. |
| 2005/0131662 A1 | 6/2005 | Ascenzi et al. |
| 2005/0137708 A1 | 6/2005 | Clark |
| 2005/0148843 A1 | 7/2005 | Roose |
| 2005/0149042 A1* | 7/2005 | Metzger ........................... 606/88 |
| 2005/0171545 A1 | 8/2005 | Walsh et al. |
| 2005/0203536 A1 | 9/2005 | Laffargue et al. |
| 2005/0203540 A1 | 9/2005 | Broyles |
| 2005/0216305 A1 | 9/2005 | Funderud |
| 2005/0222573 A1 | 10/2005 | Branch et al. |
| 2005/0234461 A1 | 10/2005 | Burdulis et al. |
| 2005/0234468 A1 | 10/2005 | Carson |
| 2005/0244239 A1 | 11/2005 | Shimp |
| 2005/0245934 A1 | 11/2005 | Tuke et al. |
| 2005/0245936 A1 | 11/2005 | Tuke et al. |
| 2005/0267353 A1 | 12/2005 | Marquart et al. |
| 2005/0267485 A1* | 12/2005 | Cordes et al. .................... 606/88 |
| 2005/0267584 A1* | 12/2005 | Burdulis et al. ............ 623/20.19 |
| 2005/0273114 A1 | 12/2005 | Novak |
| 2005/0283252 A1 | 12/2005 | Coon et al. |
| 2005/0283253 A1 | 12/2005 | Coon et al. |
| 2006/0004284 A1 | 1/2006 | Grunschlager et al. |
| 2006/0015120 A1 | 1/2006 | Richard et al. |
| 2006/0030853 A1 | 2/2006 | Haines |
| 2006/0038520 A1 | 2/2006 | Negoro et al. |
| 2006/0052725 A1 | 3/2006 | Santilli |
| 2006/0058803 A1 | 3/2006 | Cuckler et al. |
| 2006/0058884 A1 | 3/2006 | Aram et al. |
| 2006/0058886 A1 | 3/2006 | Wozencroft |
| 2006/0089621 A1 | 4/2006 | Fard |
| 2006/0093988 A1 | 5/2006 | Swaelens et al. |
| 2006/0094951 A1 | 5/2006 | Dean et al. |
| 2006/0095044 A1 | 5/2006 | Grady et al. |
| 2006/0100832 A1 | 5/2006 | Bowman |
| 2006/0111722 A1 | 5/2006 | Bouadi |
| 2006/0122616 A1 | 6/2006 | Bennett et al. |
| 2006/0136058 A1 | 6/2006 | Pietrzak |
| 2006/0142657 A1 | 6/2006 | Quaid et al. |
| 2006/0155380 A1 | 7/2006 | Clemow et al. |
| 2006/0161167 A1 | 7/2006 | Myers et al. |
| 2006/0172263 A1 | 8/2006 | Quadling et al. |
| 2006/0178497 A1 | 8/2006 | Gevaert et al. |
| 2006/0184177 A1 | 8/2006 | Echeverri |
| 2006/0190086 A1 | 8/2006 | Clemow et al. |
| 2006/0195198 A1 | 8/2006 | James |
| 2006/0204932 A1 | 9/2006 | Haymann et al. |
| 2006/0210644 A1 | 9/2006 | Levin |
| 2006/0235421 A1 | 10/2006 | Rosa et al. |
| 2006/0271058 A1 | 11/2006 | Ashton et al. |
| 2006/0276796 A1 | 12/2006 | Creger et al. |
| 2006/0276797 A1 | 12/2006 | Botimer |
| 2006/0287733 A1 | 12/2006 | Bonutti |
| 2007/0015995 A1 | 1/2007 | Lang et al. |
| 2007/0016209 A1 | 1/2007 | Ammann et al. |
| 2007/0027680 A1 | 2/2007 | Ashley et al. |
| 2007/0066917 A1 | 3/2007 | Hodorek et al. |
| 2007/0073137 A1 | 3/2007 | Schoenefeld |
| 2007/0083214 A1 | 4/2007 | Duncan et al. |
| 2007/0083266 A1 | 4/2007 | Lang |
| 2007/0100258 A1 | 5/2007 | Shoham et al. |
| 2007/0100450 A1 | 5/2007 | Hodorek |
| 2007/0100462 A1 | 5/2007 | Lang et al. |
| 2007/0118055 A1 | 5/2007 | McCombs |
| 2007/0118243 A1 | 5/2007 | Schroeder et al. |
| 2007/0150068 A1 | 6/2007 | Dong et al. |
| 2007/0156066 A1 | 7/2007 | McGinley et al. |
| 2007/0156171 A1 | 7/2007 | Lang et al. |
| 2007/0162038 A1 | 7/2007 | Tuke |
| 2007/0162039 A1 | 7/2007 | Wozencroft |
| 2007/0173946 A1 | 7/2007 | Bonutti |
| 2007/0173948 A1 | 7/2007 | Meridew et al. |
| 2007/0185498 A2 | 8/2007 | Lavallee |
| 2007/0191962 A1 | 8/2007 | Jones et al. |
| 2007/0198022 A1* | 8/2007 | Lang et al. ........................ 606/88 |
| 2007/0203430 A1 | 8/2007 | Lang et al. |
| 2007/0203605 A1 | 8/2007 | Melton et al. |
| 2007/0219639 A1 | 9/2007 | Otto et al. |
| 2007/0219640 A1 | 9/2007 | Steinberg |
| 2007/0224238 A1 | 9/2007 | Mansmann et al. |
| 2007/0226986 A1 | 10/2007 | Park et al. |
| 2007/0233121 A1* | 10/2007 | Carson et al. .................... 606/72 |
| 2007/0233136 A1 | 10/2007 | Wozencroft |
| 2007/0233140 A1 | 10/2007 | Metzger et al. |
| 2007/0233141 A1* | 10/2007 | Park et al. ........................ 606/88 |
| 2007/0233269 A1 | 10/2007 | Steines et al. |
| 2007/0233272 A1 | 10/2007 | Boyce et al. |
| 2007/0238069 A1 | 10/2007 | Lovald et al. |
| 2007/0239282 A1 | 10/2007 | Caylor et al. |
| 2007/0239481 A1 | 10/2007 | DiSilvestro et al. |
| 2007/0250169 A1 | 10/2007 | Lang |
| 2007/0253617 A1 | 11/2007 | Arata et al. |
| 2007/0255288 A1 | 11/2007 | Mahfouz et al. |
| 2007/0255412 A1 | 11/2007 | Hajaj et al. |
| 2007/0262867 A1 | 11/2007 | Westrick et al. |
| 2007/0272747 A1 | 11/2007 | Woods et al. |
| 2007/0276224 A1 | 11/2007 | Lang et al. |
| 2007/0276400 A1 | 11/2007 | Moore et al. |
| 2007/0276501 A1 | 11/2007 | Betz et al. |
| 2007/0288030 A1 | 12/2007 | Metzger et al. |
| 2008/0009952 A1 | 1/2008 | Hodge |
| 2008/0015605 A1 | 1/2008 | Collazo |
| 2008/0021299 A1 | 1/2008 | Meulink |
| 2008/0021494 A1 | 1/2008 | Schmelzeisen-Redeker et al. |
| 2008/0021567 A1 | 1/2008 | Meulink et al. |
| 2008/0027563 A1 | 1/2008 | Johnson et al. |

| | | | | | | |
|---|---|---|---|---|---|---|
| 2008/0033442 A1 | 2/2008 | Amiot et al. | | 2009/0177282 A1 | 7/2009 | Bureau et al. |
| 2008/0051910 A1 | 2/2008 | Kammerzell et al. | | 2009/0187193 A1 | 7/2009 | Maroney et al. |
| 2008/0058945 A1 | 3/2008 | Hajaj et al. | | 2009/0209884 A1 | 8/2009 | Van Vorhis et al. |
| 2008/0058947 A1 | 3/2008 | Earl et al. | | 2009/0209961 A1 | 8/2009 | Ferrante et al. |
| 2008/0062183 A1 | 3/2008 | Swaelens | | 2009/0222014 A1 | 9/2009 | Bojarski et al. |
| 2008/0065225 A1 | 3/2008 | Wasielewski et al. | | 2009/0222015 A1 | 9/2009 | Park et al. |
| 2008/0112996 A1 | 5/2008 | Harlow et al. | | 2009/0222016 A1 | 9/2009 | Park et al. |
| 2008/0114370 A1 | 5/2008 | Schoenefeld | | 2009/0222103 A1 | 9/2009 | Fitz et al. |
| 2008/0133022 A1 | 6/2008 | Caylor | | 2009/0228016 A1 | 9/2009 | Alvarez et al. |
| 2008/0140209 A1 | 6/2008 | Iannotti et al. | | 2009/0234360 A1 | 9/2009 | Alexander |
| 2008/0146969 A1 | 6/2008 | Kurtz | | 2009/0248044 A1 | 10/2009 | Amiot et al. |
| 2008/0147072 A1 | 6/2008 | Park et al. | | 2009/0254093 A1 | 10/2009 | White et al. |
| 2008/0172125 A1 | 7/2008 | Ek | | 2009/0254367 A1 | 10/2009 | Belcher et al. |
| 2008/0195099 A1 | 8/2008 | Minas | | 2009/0270868 A1 | 10/2009 | Park et al. |
| 2008/0195107 A1 | 8/2008 | Cuckler et al. | | 2009/0274350 A1 | 11/2009 | Pavlovskaia et al. |
| 2008/0195108 A1 | 8/2008 | Bhatnagar et al. | | 2009/0306676 A1 | 12/2009 | Lang et al. |
| 2008/0195216 A1 | 8/2008 | Philipp | | 2009/0307893 A1 | 12/2009 | Burdulis, Jr. et al. |
| 2008/0200926 A1 | 8/2008 | Verard et al. | | 2009/0318836 A1 | 12/2009 | Stone et al. |
| 2008/0208200 A1 | 8/2008 | Crofford | | 2010/0016984 A1 | 1/2010 | Trabish |
| 2008/0208353 A1 | 8/2008 | Kumar et al. | | 2010/0016986 A1 | 1/2010 | Trabish |
| 2008/0215059 A1 | 9/2008 | Carignan et al. | | 2010/0023015 A1 | 1/2010 | Park |
| 2008/0230422 A1 | 9/2008 | Pleil et al. | | 2010/0030231 A1 | 2/2010 | Revie et al. |
| 2008/0234664 A1 | 9/2008 | May et al. | | 2010/0042105 A1 | 2/2010 | Park et al. |
| 2008/0234683 A1 | 9/2008 | May | | 2010/0049195 A1 | 2/2010 | Park et al. |
| 2008/0234685 A1 | 9/2008 | Gjerde | | 2010/0076439 A1 | 3/2010 | Hatch |
| 2008/0234833 A1 | 9/2008 | Bandoh et al. | | 2010/0076505 A1 | 3/2010 | Borja |
| 2008/0243127 A1* | 10/2008 | Lang et al. ............... 606/87 | | 2010/0076563 A1 | 3/2010 | Otto et al. |
| 2008/0255674 A1 | 10/2008 | Rahaman et al. | | 2010/0076571 A1 | 3/2010 | Hatch |
| 2008/0257363 A1 | 10/2008 | Schoenefeld et al. | | 2010/0082034 A1 | 4/2010 | Remia |
| 2008/0262500 A1* | 10/2008 | Collazo .................... 606/88 | | 2010/0082035 A1 | 4/2010 | Keefer |
| 2008/0262624 A1 | 10/2008 | White et al. | | 2010/0087829 A1 | 4/2010 | Metzger et al. |
| 2008/0269906 A1 | 10/2008 | Iannotti et al. | | 2010/0094295 A1 | 4/2010 | Schnieders et al. |
| 2008/0275452 A1 | 11/2008 | Lang et al. | | 2010/0105011 A1 | 4/2010 | Karkar et al. |
| 2008/0281328 A1 | 11/2008 | Lang et al. | | 2010/0121335 A1 | 5/2010 | Penenberg et al. |
| 2008/0281329 A1 | 11/2008 | Fitz et al. | | 2010/0137869 A1 | 6/2010 | Borja et al. |
| 2008/0281426 A1 | 11/2008 | Fitz et al. | | 2010/0137924 A1 | 6/2010 | Tuke et al. |
| 2008/0287954 A1 | 11/2008 | Kunz et al. | | 2010/0145343 A1 | 6/2010 | Johnson et al. |
| 2008/0294266 A1 | 11/2008 | Steinberg | | 2010/0145344 A1 | 6/2010 | Jordan et al. |
| 2008/0300600 A1 | 12/2008 | Guelat et al. | | 2010/0152782 A1 | 6/2010 | Stone et al. |
| 2008/0306558 A1 | 12/2008 | Hakki | | 2010/0160917 A1 | 6/2010 | Fitz et al. |
| 2008/0312659 A1 | 12/2008 | Metzger et al. | | 2010/0168754 A1 | 7/2010 | Fitz et al. |
| 2008/0319448 A1 | 12/2008 | Lavallee et al. | | 2010/0168857 A1 | 7/2010 | Hatch |
| 2009/0012526 A1 | 1/2009 | Fletcher | | 2010/0179663 A1 | 7/2010 | Steinberg |
| 2009/0018546 A1 | 1/2009 | Daley | | 2010/0185202 A1 | 7/2010 | Lester et al. |
| 2009/0018666 A1 | 1/2009 | Grundei et al. | | 2010/0191244 A1 | 7/2010 | White et al. |
| 2009/0024131 A1 | 1/2009 | Metzger et al. | | 2010/0212138 A1 | 8/2010 | Carroll et al. |
| 2009/0043556 A1 | 2/2009 | Axelson et al. | | 2010/0217109 A1 | 8/2010 | Belcher |
| 2009/0076371 A1 | 3/2009 | Lang et al. | | 2010/0217270 A1 | 8/2010 | Polinski et al. |
| 2009/0076512 A1 | 3/2009 | Ammann et al. | | 2010/0217336 A1 | 8/2010 | Crawford et al. |
| 2009/0082770 A1 | 3/2009 | Worner et al. | | 2010/0217338 A1 | 8/2010 | Carroll et al. |
| 2009/0087276 A1 | 4/2009 | Rose | | 2010/0228257 A1 | 9/2010 | Bonutti |
| 2009/0088674 A1 | 4/2009 | Caillouette et al. | | 2010/0249657 A1 | 9/2010 | Nycz et al. |
| 2009/0088753 A1 | 4/2009 | Aram et al. | | 2010/0249796 A1 | 9/2010 | Nycz |
| 2009/0088754 A1 | 4/2009 | Aker et al. | | 2010/0262150 A1 | 10/2010 | Lian |
| 2009/0088755 A1 | 4/2009 | Aker et al. | | 2010/0274253 A1 | 10/2010 | Ure |
| 2009/0088758 A1 | 4/2009 | Bennett | | 2010/0281678 A1 | 11/2010 | Burdulis, Jr. et al. |
| 2009/0088759 A1* | 4/2009 | Aram et al. ............... 606/87 | | 2010/0286700 A1 | 11/2010 | Snider et al. |
| 2009/0088760 A1 | 4/2009 | Aram et al. | | 2010/0292743 A1 | 11/2010 | Singhal et al. |
| 2009/0088761 A1 | 4/2009 | Roose et al. | | 2010/0305574 A1 | 12/2010 | Fitz et al. |
| 2009/0088763 A1 | 4/2009 | Aram et al. | | 2010/0324692 A1 | 12/2010 | Uthgenannt et al. |
| 2009/0088865 A1 | 4/2009 | Brehm | | 2011/0004317 A1 | 1/2011 | Hacking et al. |
| 2009/0088866 A1 | 4/2009 | Case | | 2011/0015636 A1 | 1/2011 | Katrana et al. |
| 2009/0089034 A1 | 4/2009 | Penney et al. | | 2011/0015639 A1 | 1/2011 | Metzger et al. |
| 2009/0089081 A1 | 4/2009 | Haddad | | 2011/0015752 A1 | 1/2011 | Meridew |
| 2009/0093816 A1 | 4/2009 | Roose et al. | | 2011/0029091 A1 | 2/2011 | Bojarski et al. |
| 2009/0096613 A1 | 4/2009 | Westrick | | 2011/0029116 A1 | 2/2011 | Jordan et al. |
| 2009/0099567 A1 | 4/2009 | Zajac | | 2011/0046735 A1 | 2/2011 | Metzger et al. |
| 2009/0105837 A1 | 4/2009 | Lafosse et al. | | 2011/0054478 A1 | 3/2011 | Vanasse et al. |
| 2009/0118736 A1 | 5/2009 | Kreuzer | | 2011/0066193 A1 | 3/2011 | Lang et al. |
| 2009/0131941 A1 | 5/2009 | Park et al. | | 2011/0071528 A1 | 3/2011 | Carson |
| 2009/0131942 A1 | 5/2009 | Aker et al. | | 2011/0071529 A1 | 3/2011 | Carson |
| 2009/0138020 A1 | 5/2009 | Park et al. | | 2011/0071530 A1 | 3/2011 | Carson |
| 2009/0149965 A1 | 6/2009 | Quaid | | 2011/0071532 A1 | 3/2011 | Carson |
| 2009/0149977 A1 | 6/2009 | Schendel | | 2011/0071533 A1 | 3/2011 | Metzger et al. |
| 2009/0151736 A1 | 6/2009 | Belcher et al. | | 2011/0092804 A1 | 4/2011 | Schoenefeld et al. |
| 2009/0157083 A1 | 6/2009 | Park et al. | | 2011/0093086 A1 | 4/2011 | Witt et al. |
| 2009/0163922 A1 | 6/2009 | Meridew et al. | | 2011/0151027 A1 | 6/2011 | Clineff et al. |
| 2009/0163923 A1 | 6/2009 | Flett et al. | | 2011/0151259 A1 | 6/2011 | Jarman-Smith et al. |
| 2009/0164024 A1 | 6/2009 | Rudan et al. | | 2011/0153025 A1 | 6/2011 | McMinn |

| | | | |
|---|---|---|---|
| 2011/0160736 A1 | 6/2011 | Meridew et al. | |
| 2011/0160867 A1 | 6/2011 | Meridew et al. | |
| 2011/0166578 A1 | 7/2011 | Stone et al. | |
| 2011/0172672 A1 | 7/2011 | Dubeau et al. | |
| 2011/0184419 A1 | 7/2011 | Meridew et al. | |
| 2011/0184526 A1 | 7/2011 | White et al. | |
| 2011/0190899 A1 | 8/2011 | Pierce et al. | |
| 2011/0190901 A1 | 8/2011 | Weissberg et al. | |
| 2011/0213376 A1 | 9/2011 | Maxson et al. | |
| 2011/0218545 A1 | 9/2011 | Catanzarite et al. | |
| 2011/0224674 A1 | 9/2011 | White et al. | |
| 2011/0257657 A1 | 10/2011 | Turner et al. | |
| 2012/0101586 A1 | 4/2012 | Carson | |

FOREIGN PATENT DOCUMENTS

| | | | |
|---|---|---|---|
| CA | 2501041 A1 | 4/2004 | |
| CA | 2505371 A1 | 5/2004 | |
| CA | 2505419 A1 | 6/2004 | |
| CA | 2506849 A1 | 6/2004 | |
| CA | 2546958 A1 | 6/2005 | |
| CA | 2546965 A1 | 6/2005 | |
| CA | 2588907 A1 | 6/2006 | |
| CA | 2590534 A1 | 6/2006 | |
| CN | 1630495 A | 6/2005 | |
| CN | 1728976 A | 2/2006 | |
| CN | 1729483 A | 2/2006 | |
| CN | 1729484 A | 2/2006 | |
| CN | 1913844 A | 2/2007 | |
| CN | 101111197 A | 1/2008 | |
| DE | 3447365 A1 | 7/1986 | |
| DE | 04219939 A1 | 12/1993 | |
| DE | 4421153 A1 | 12/1995 | |
| DE | 102009028503 A1 | 2/2011 | |
| EP | 0114505 A1 | 8/1984 | |
| EP | 0326768 A2 | 8/1989 | |
| EP | 0579868 A2 | 1/1994 | |
| EP | 0645984 A1 | 4/1995 | |
| EP | 0650706 A1 | 5/1995 | |
| EP | 0916324 A2 | 5/1999 | |
| EP | 1321107 A1 | 6/2003 | |
| EP | 1327424 A1 | 7/2003 | |
| EP | 1437102 A1 | 7/2004 | |
| EP | 01486900 A1 | 12/2004 | |
| EP | 1852072 A2 | 7/2007 | |
| EP | 1832239 A1 | 9/2007 | |
| FR | 2659226 A1 | 9/1991 | |
| FR | 2721195 A1 | 12/1995 | |
| FR | 2768916 A1 | 4/1999 | |
| GB | 2094590 A | 9/1982 | |
| GB | 2197790 A | 6/1988 | |
| GB | 2442441 A | 4/2008 | |
| JP | 59157715 A | 9/1984 | |
| JP | 60231208 A | 11/1985 | |
| KR | 20050072500 A | 7/2005 | |
| KR | 20050084024 A | 8/2005 | |
| RU | 2083179 C1 | 7/1997 | |
| RU | 2113182 C1 | 6/1998 | |
| RU | 2125835 C1 | 2/1999 | |
| RU | 2138223 C1 | 9/1999 | |
| RU | 2175534 C2 | 11/2001 | |
| RU | 2187975 C1 | 8/2002 | |
| TW | 231755 | 5/2005 | |
| WO | WO-8807840 A1 | 10/1988 | |
| WO | WO-9107139 A1 | 5/1991 | |
| WO | WO-9325157 A1 | 12/1993 | |
| WO | WO-9528688 A1 | 10/1995 | |
| WO | WO-9952473 A1 | 10/1999 | |
| WO | WO-9959106 A1 | 11/1999 | |
| WO | WO-0170142 A1 | 9/2001 | |
| WO | WO-0184479 A1 | 11/2001 | |
| WO | WO-0217821 A2 | 3/2002 | |
| WO | WO-0226145 | 4/2002 | |
| WO | WO-0236024 A1 | 5/2002 | |
| WO | WO-02096268 A2 | 12/2002 | |
| WO | WO-03051210 A2 | 6/2003 | |
| WO | WO-03051211 A1 | 6/2003 | |
| WO | WO-2004032806 A1 | 4/2004 | |
| WO | WO-2004049981 A2 | 6/2004 | |
| WO | WO-2004051301 A2 | 6/2004 | |
| WO | WO-2004078069 A2 | 9/2004 | |
| WO | WO-2005051239 A1 | 6/2005 | |
| WO | WO-2005051240 A1 | 6/2005 | |
| WO | WO-2005077039 A2 | 8/2005 | |
| WO | WO-2006058057 A2 | 6/2006 | |
| WO | WO-2006060795 A1 | 6/2006 | |
| WO | WO-2006092600 A1 | 9/2006 | |
| WO | WO-2006127486 A2 | 11/2006 | |
| WO | WO-2006134345 A1 | 12/2006 | |
| WO | WO-2006136955 A1 | 12/2006 | |
| WO | WO-2007041375 A2 | 4/2007 | |
| WO | WO-2007053572 A2 | 5/2007 | |
| WO | WO-2007062079 A2 | 5/2007 | |
| WO | WO-2007092841 A2 | 8/2007 | |
| WO | WO-2007137327 A1 | 12/2007 | |
| WO | WO-2007145937 A2 | 12/2007 | |
| WO | WO-2008014618 A1 | 2/2008 | |
| WO | WO-2008021494 A2 | 2/2008 | |
| WO | WO-2008040961 A1 | 4/2008 | |
| WO | WO-2008044055 A1 | 4/2008 | |
| WO | WO-2008101090 A2 | 8/2008 | |
| WO | WO-2008112996 A1 | 9/2008 | |
| WO | WO-2008140748 A1 | 11/2008 | |
| WO | WO-2009001083 A1 | 12/2008 | |
| WO | WO-2009025783 A1 | 2/2009 | |
| WO | WO-2011018458 A1 | 2/2011 | |

OTHER PUBLICATIONS

International Preliminary Report and Written Opinion mailed Jan. 5, 2012 for PCT/US2010/038845 claiming benefit of U.S. Appl. No. 12/486,992, filed Jun. 18, 2009.

International Preliminary Report on Patentability and Written Opinion mailed Dec. 22, 2011 for PCT/US2010/038177 claiming benefit of U.S. Appl. No. 12/483,807, filed Jun. 12, 2009.

International Search Report mailed Nov. 30, 2010 for PCT/EP2010/061630 filed Aug. 10, 2010 claiming benefit of DE102009028503.2 filed Aug. 13, 2009.

Supplementary European Search Report mailed Nov. 15, 2011 for EP07809326, which claims benefit of PCT/US2007/013223, filed Jun. 5, 2007; which claims priority to U.S. Appl. No. 11/756,057, filed May 31, 2007.

International Search Report and Written Opinion for PCT/US2009/056670 mailed Mar. 2, 2010 claiming benefit of U.S. Appl. No. 12/211,407, filed Sep. 16, 2008 (which is a CIP of U.S. Appl. No. 12/039,849, filed Feb. 29, 2008, which is a CIP of U.S. Appl. No. 11/971,390, filed Jan. 9, 2008, which is a CIP of U.S. Appl. No. 11/756,957, filed May 31, 2007).

International Search Report and Written Opinion mailed Apr. 22, 2010 for PCT/US2010/024579 claiming benefit of U.S. Appl. No. 12/389,930, filed Feb. 20, 2009.

Lombardi, Adolph, et al., "Patient-Specific Approach in Total Knee Arthroplasty," Knee Orthopedics, ORTHOSuperSite (Sep. 1, 2008), 5 pages, http://www.orthosupersite.com/view.aspx?rid=31419, printed May 20, 2010.

International Preliminary Report on Patentability mailed Aug. 25, 2011 for PCT/US2010/024073 filed Feb. 12, 2010, claiming benefit of U.S. Appl. No. 12/371,096, filed Feb. 13, 2009.

International Preliminary Report on Patentability mailed Sep. 1, 2011 for PCT/US2010/024579 claiming benefit of U.S. Appl. No. 12/389,930, filed Feb. 20, 2009.

International Preliminary Report on Patentability mailed Sep. 1, 2011 for PCT/US2010/024584 claiming benefit of U.S. Appl. No. 12/389,901, filed Feb. 20, 2009.

International Search Report and Written Opinion mailed Aug. 9, 2011 for PCT/US2011/026333 claiming benefit of U.S. Appl. No. 12/714,023, filed Feb. 26, 2010.

International Preliminary Report on Patentability for PCT/US2007/013223 mailed Dec. 24, 2008 claiming benefit of U.S. Appl. No. 11/756,057, filed May 31, 2007.

International Search Report and Written Opinion mailed Jun. 4, 2010 for PCT/US2010/024073 filed Feb. 12, 2010, claiming benefit of U.S. Appl. No. 12/371,096, filed Feb. 13, 2009.

International Search Report and Written Opinion mailed Jun. 10, 2010 for PCT/US2010/038177 claiming benefit of U.S. Appl. No. 12/483,807, filed Jun. 12, 2009.

International Preliminary Report on Patentability and Written Opinion mailed Oct. 28, 2010 for PCT/US2009/039507 claiming benefit of U.S. Appl. No. 12/103,824, filed Apr. 16, 2008.
International Search Report and Written Opinion mailed Dec. 7, 2010 for PCT/US2010/050701 claiming benefit of U.S. Appl. No. 12/571,969, filed Oct. 1, 2009.
International Search Report and Written Opinion mailed Oct. 5, 2010 for PCT/US2010/038845 claiming benefit of U.S. Appl. No. 12/486,992, filed Jun. 18, 2009.
International Search Report and Written Opinion mailed Aug. 19, 2010 for PCT/US2010/024584 claiming benefit of U.S. Appl. No. 12/389,901, filed Feb. 20, 2009.
International Preliminary Report on Patentability mailed Mar. 31, 2011 for PCT/US2009/056670 claiming benefit of U.S. Appl. No. 12/211,407, filed Sep. 16, 2008.
Invitation to Pay Additional Fees mailed May 3, 2011 for PCT/US2011/026333 claiming benefit of U.S. Appl. No. 12/714,023, filed Feb. 26, 2010.
International Preliminary Report on Patentability and Written Opinion for PCT/US2009/039578 mailed Oct. 28, 2010 claiming benefit of U.S. Appl. No. 12/103,834, filed Apr. 16, 2008.
International Search Report and Written Opinion mailed May 9, 2011 for PCT/US2011/026412 claiming benefit of U.S. Appl. No. 12/872,663, filed Aug. 31, 2010.
"Customized Patient Instruments, Patient specific instruments for patient specific needs," brochure. (2008) DePuy Orthopaedics, Inc. 14 sheets.
"Customized Patient Instruments, Primary Cruciate Retaining Surgical Technique for use with the Sigma® Knee System Utilizing Specialist® 2 Instrumentation," brochure. (2008) DePuy Orthopaedics, Inc. pp. 1-23.
"TruMatch™ Personalized knee replacement solutions," tri-fold brochure. (2009) SIGMA® DePuy Orthopaedics, Inc. 2 pages.
Kelly, Todd C., M.D., "Role of Navigation in Total Hip Arthroplasty." The Journal of Bone & Joint Surgery(2009) pp. 153-158. vol. 91-A, Supplement 1.
"Zimmer® UniSpacer® Knee System," brochure. (2005) Zimmer, Inc. 4 sheets.
"Method for constructing an allograft sleeve." Research Disclosure (Dec. 2003) No. 476, p. 1294.
"Signature™ Personalized Patient Care, Surgical Technique Addendum to the Vanguard Knee System" brochure. Biomet® Orthopedics, Inc. (2009) pp. 1-8.
"Knee tensor combined with laser femoral head locator," Research Disclosure. Jul. 2006. No. 507; p. 903.
"Discovery® Elbow System," brochure. Biomet Orthopedics, Inc. (2007) 3 sheets.
"Discovery® Elbow System Surgical Technique," brochure. Biomet Orthopedics, Inc. (2008) pp. 1-25.
Radermacher, Klaus, et al. "Computer Assisted Orthopaedic Individual Templates." Clinical Orthopaedics and Related Research. (Sep. 1998) No. 354; pp. 28-38.
Cohen, Zohara A., et al. "Knee cartilage topography, thickness, and contact areas from MRI: in-vitro calibration and in-vivo measurements." Journal of the OsteoArthritis Research Society International. Osteoarthritis and Cartilage, (1999) vol. 7; No. 1 pp. 95-109.
"Ascent Total Knee System," brochure. Biomet, Inc. (1999) 16 sheets.
"Regenerex® Tibial Cone Augment, Surgical Technique Addendum to the Vanguard® SSK Revision System," brochure. Biomet® Orthopedics. (2009) pp. 1-8 (12 sheets).
"OSS™ Orthopaedic Salvage System, Femoral/Tibial Augmentation," brochure. Biomet Orthopedics, Inc., (2003) pp. 1-8 (12 sheets).
"Vanguard® PFR Partial Knee Patellofemoral Replacement System," Surgical Technique brochure. Biomet Orthopaedics, (2010) pp. 1-25.
"Amazing Precision. Beautiful Results. The next evolution of MAKOplasty® is here," brochure. (Feb. 2009) MAKO Surgical Corp. 6 pages.
"Hipsextant Instructions of Use." (2011) Surgical Planning Associates, Inc. 19 pages.

Murphy, S.B., et al. "The Hip Sextant: Navigation of Acetabular Component Orientation Using a Mechanical Instrument," brochure. (2009) 1 page.
"Patient Matched PMI Implants, C.A.M.R.A. 3-D Imaging," brochure, Biomet, Inc. (1990) 6 pages.
Birnbaum, Klaus, M.D., "Computer-Assisted Orthopedic Surgery With Individual Templates and Comparison to Conventional Method," SPINE vol. 26, No. 4, pp. 365-370 (2001) Lippincott Williams & Wilkins, Inc.
Botha, Charl P., Technical Report: DeVIDE—The Delft Visualisation and Image processing Development Environment, pp. 1-49 (May 31, 2006).
Eckhoff, Donald G., et al., "Three-Dimensional Mechanics, Kinematics, and Morphology of the Knee Viewed in Virtual Reality," The Journal of Bone & Joint Surgery, vol. 81 (Dec. 4, 2005) pp. 71-80.
Fortin, Thomas, D.D.S., Ph.D., et al., "Precise Dental Implant Placement in Bone Using Surgical Guides in Conjunction with Medical Imaging Techniques," Journal of Oral Implantology, Clinical, vol. 26, No. 4 (2000) pp. 300-303.
Haaker, R.G., et al., "Minimal-invasive navigiert implantierte unikondyläre Knieendoprothese," Orthopäde 2006 35:1073-1079 (2006) Spinger Medizin Verlag.
Hafez, M.A., et al., "Computer-assisted Total Knee Arthroplasty Using Patient-specific Templating," Clinical Orthopaedics and Related Research, No. 444 (pp. 184-192) 2006 Lippincott Williams & Wilkins.
Hazan, Eric J., M.D., "Computer-Assisted Orthopaedic Sugery, A New Paradigm," Techniques in Orthopaedics® vol. 18, No. 2, (2003) pp. 221-229.
Hutmacher, Dietmar, W., "Scaffolds in tissue engineering bone and cartilage," Biomaterials, 2000 Elsevier Science Ltd. (pp. 2529-2543).
International Preliminary Report on Patentability for PCT/US2007/013223 issued Nov. 26, 2007.
International Search Report and Written Opinion for PCT/US2007/013223 mailed Nov. 26, 2007.
International Search Report and Written Opinion for PCT/US2009/039507 mailed Jul. 14, 2009.
International Search Report and Written Opinion for PCT/US2009/039578 mailed Jul. 31, 2009.
Invitation to Pay Additional Fees with Partial International Search mailed Nov. 26, 2009 for PCT/US2009/056670.
Kaus, Michael R., Ph.D., "Automated Segmentation of MR Images of Brain Tumors," Radiology, vol. 218, No. 2, (2001) pp. 586-591.
Klein, M., "Robot assisted insertion of craniofacial implants—clinical experience," CARS 2001, pp. 133-138 (2001) Elsevier Science B.V.
Lynch, John A., et al., "Cartilage segmentation of 3D MRI scans of the osteoarthritic knee combining user knowledge and active contours," Medical Imaging 2000: Image Processing SPIE vol. 3979 (2000) pp. 925-935.
Nicholls, Paul, M.D., "Trauma Grand Rounds PMI (Patient-Matched Implants)" brochure, Biomet Orthopedics, Inc., (Feb. 29, 2000) 1 page.
Overhoff, H.M., et al., "Total Knee Arthroplasty: Coordinate System Definition and Planning based on 3-D Ultrasound Image Volumes," CARS 2001, pp. 283-288, (2001) Elsevier Science B.V.
Portheine, F., "CT-basierte Planung und DISOS-Schablonennavigation in der Kniegelenkendoprothetik," in Navigation und Robotic in der Gelenk—und Wirbelsäulenchirugie, Kapitel 32, Springer Verlag (2003) pp. 262-269.
Portheine, F., et al., Entwicklung eines klinischen Demonstrators für die computerunterstützte Orthopädische Chirurgie mit CT-Bildbasierten Individualschablonen, Bildverarbeitung fur die Medizin (1998) 5 pages.
Portheine, K., "Development of a clinical demonstrator for computer assisted orthopedic surgery with CT-image based individual templates," Computer Assisted Radiology and Surgery, pp. 944-949, (1997) Elsevier Science B.V.
Radermacher, "Computer Assisted Orthopaedic Surgery with Image Based Individual Templates," Clinical Orthopaedics and Related Research No. 354, pp. 28-38 (1998) Lippincott Williams & Wilkins.

Radermacher, K., et al., "Computer Integrated Orthopaedic Surgery: Connection of Planning and Execution in Surgical Intervention," Computer-integrated surgery: technology and clinical applications, (1996) pp. 451-463.

Radermacher, K., et al., "CT Image-Based Planning and Execution of Interventions in Orthopedic Surgery Using Individual Templates, Experimental Results and Aspects of Clinical Applications," Computer Assisted Orthopedic Surgery (CAOS), pp. 42-52, (1995) Hogrefe & Huber Publishers.

Radermacher, K., et al., "Image Guided Orthopedic Surgery Using Individual Templates," Springer Berlin/Heidelberg, CVRMed-MRCAS'97, vol. 1205/1997 pp. 606-615).

Radermacher, K., et al., "Technique for Better Execution of CT Scan Planned Orthopedic Surgery on Bone Structures," Supplied by the British Library—"The world's knowledge" 2nd Congress of ISCAS Conference in Berlin Germany (Jun. 1995) pp. 933-938.

Schuller-Götzburg, P., et al., 3D-Implantatplanung and Stereolithographie-Implantatbohrschablonen, Stomatologie 101.3, pp. 55-59 (2004).

Sharp, S. Michael, Ph.D., Patient-Specific, Resurfacing Bi-Compartmental Arthuroplasty, Futuretech, Orthopaedic Product News (Mar./Apr. 2008) pp. 12-15.

Sisto, Domenick, J., et al., "Custom Patellofemoral Arthroplasty of the Knee Surgical Technique," Journal of Bone and Joint Surgery, vol. 89-A, pp. 214-225 (2007).

Slammin, John et al, "Do You Have This Implant in My Size?", MDT Medical Design Technology, 3 pages, http://www.mdtmag.com/scripts/ShowPR.asp?PUBCODE=046&ACCT=0007796&Issue... accessed Jul. 31, 2008.

Steinwachs, Matthias Reinhard, "Cartilage Repair—Autologous Chondrocyte Transplantation and Autologous Matrix-induced Chondrogenesis," European Musculoskeletal Review (2006) pp. 65-68.

International Preliminary Report on Patentability for PCT/US2010/050701 mailed Apr. 12, 2012 claiming benefit of U.S. Appl. No. 12/571,969, filed Oct. 1, 2009.

International Search Report and Written Opinion mailed Mar. 5, 2012 for PCT/US2011/057300 claiming benefit of U.S. Appl. No. 12/938,905, filed Nov. 3, 2010.

International Search Report and Written Opinion mailed May 8, 2012 for PCT/US2012/026356 claiming benefit of U.S. Appl. No. 13/041,883, filed Mar. 7, 2011.

Thoma, W., et al., "Endoprothetischen Versorgung des Kniegelenks auf der Basis eines 3D-computertomographischen Subtraktionverfahrens," Zuma Thema: Computergestützte orthopädische Chirugie, Der Orthopäde 29:641-644 Springer-Verlag (Jul. 2000) Translation provided: Thoma, W., "Endoprosthetic care of the knee joint based on a 3D computer chromatography subtraction process," Topic: Computer-aided orthopedic surgery. Orthopedist 2000 29:641-644 Springer Verlag (Jul. 2000).

* cited by examiner

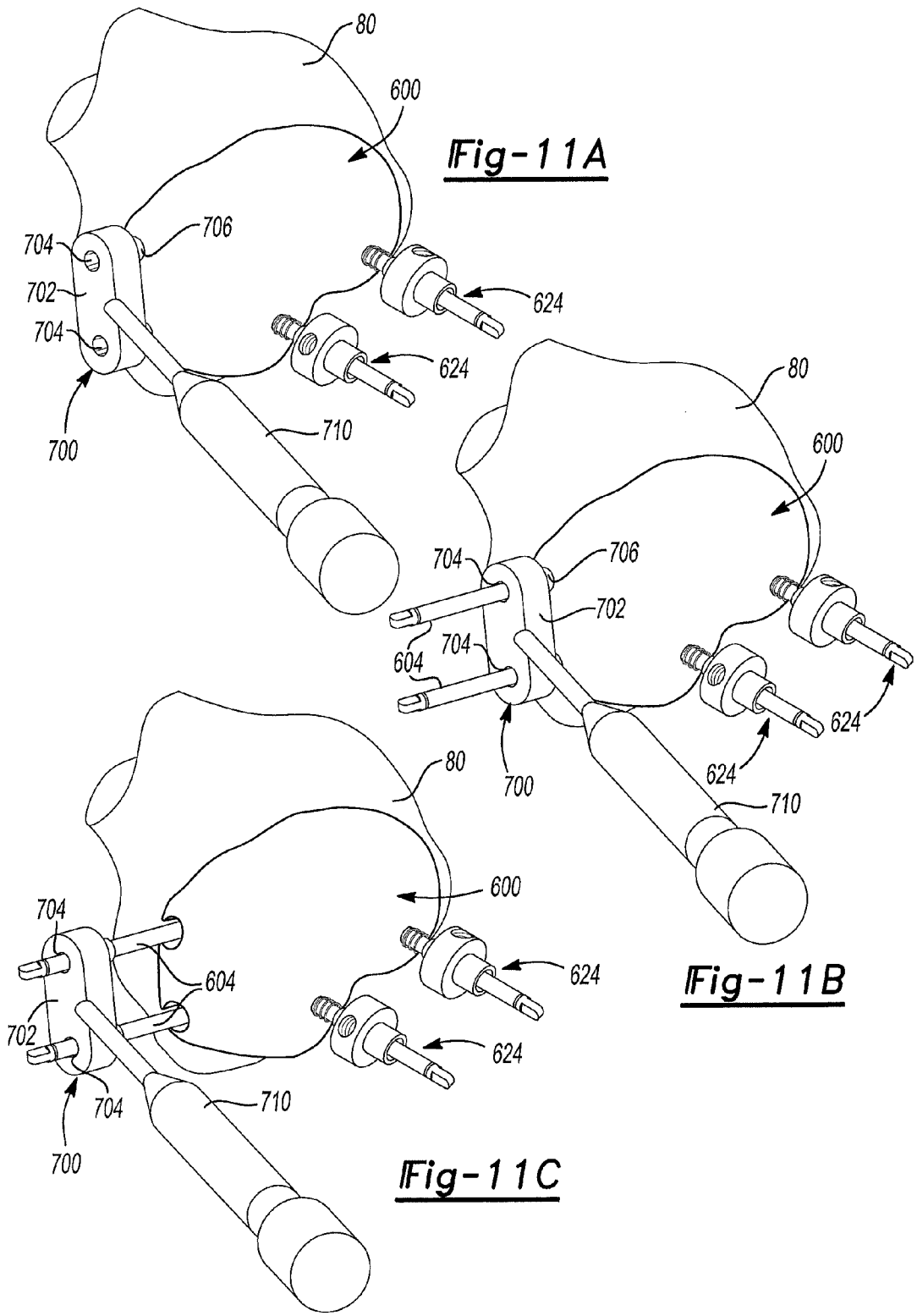

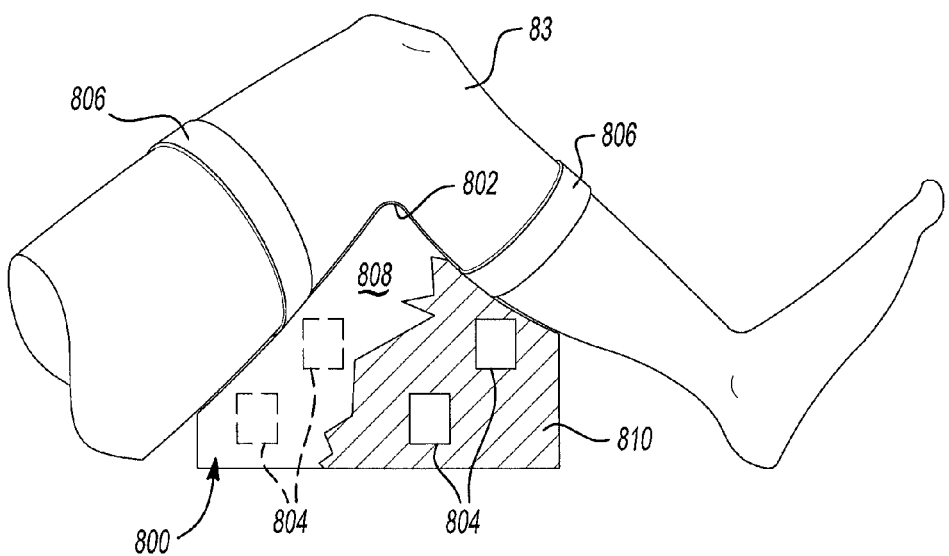
Fig-17
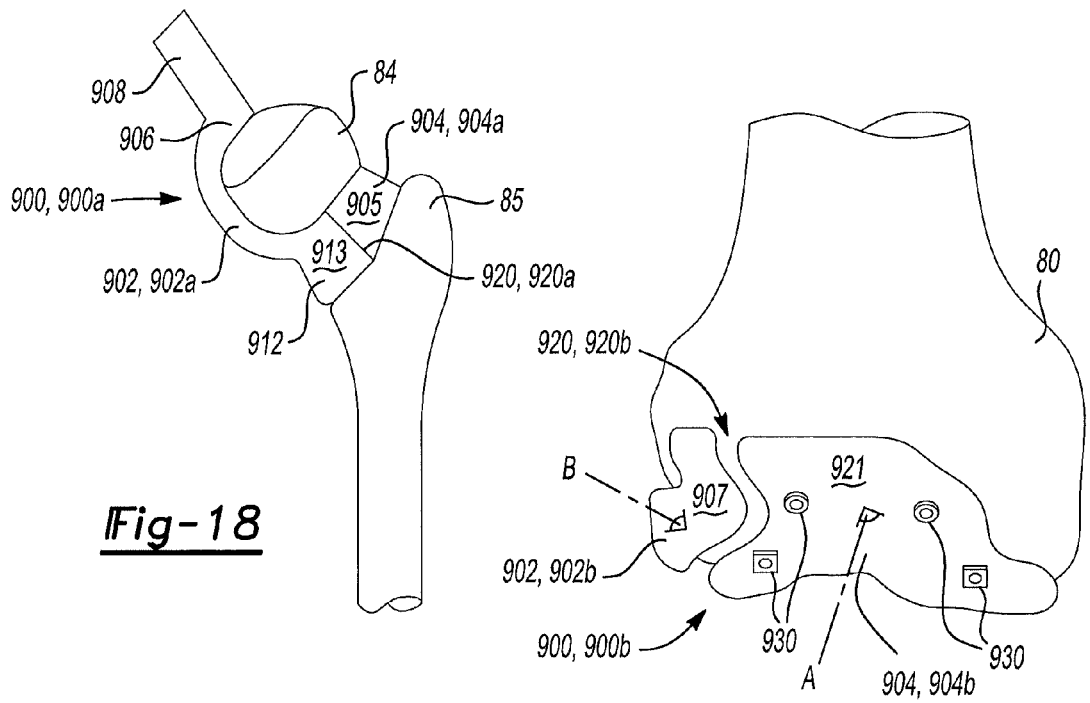
Fig-18
Fig-19

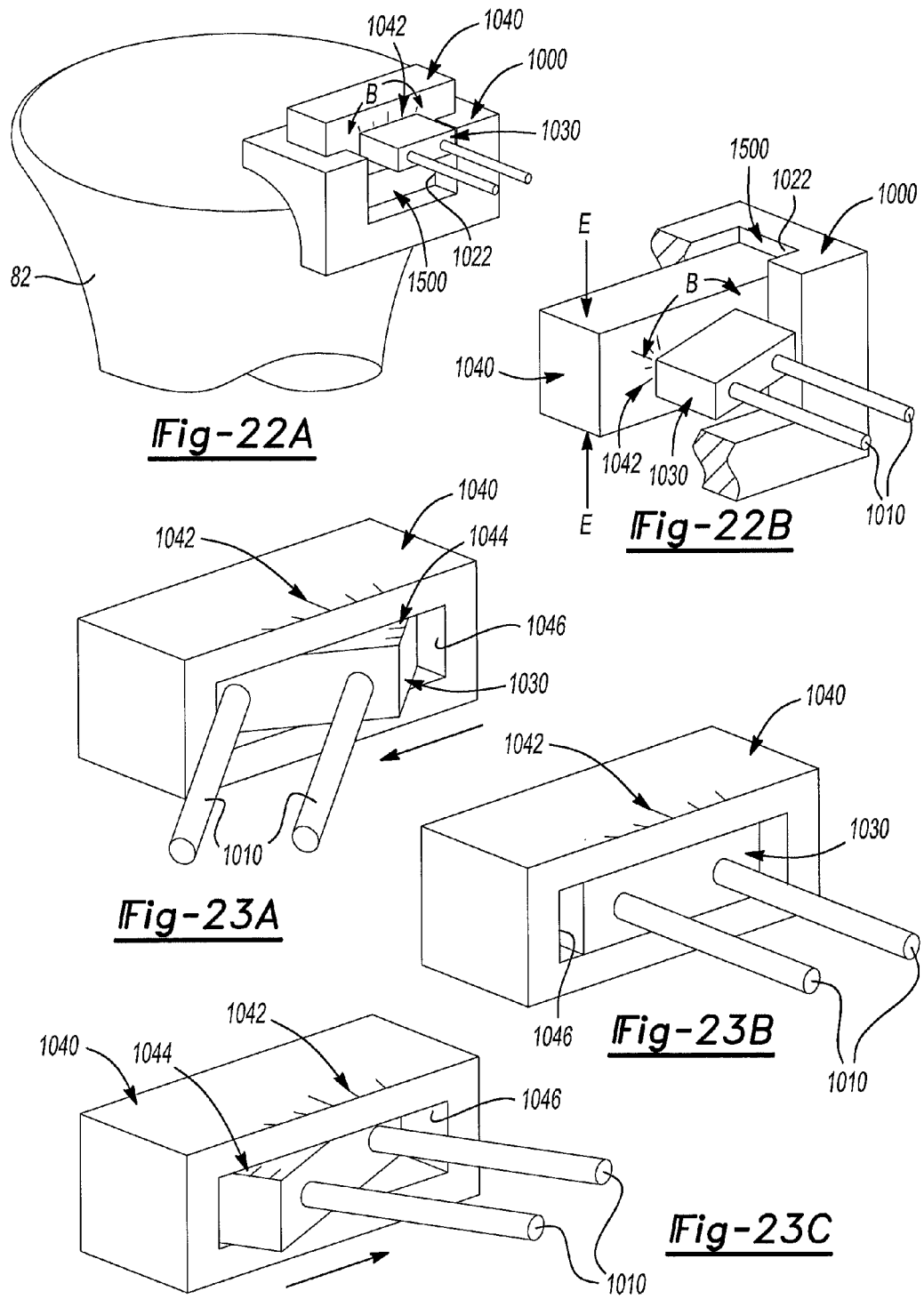

PATIENT SPECIFIC KNEE ALIGNMENT GUIDE AND ASSOCIATED METHOD

CROSS-REFERENCE TO RELATED APPLICATIONS

This application is a continuation-in part of U.S. application Ser. No. 11/756,057, filed on May 31, 2007, which claims the benefit of U.S. Provisional Application No. 60/812,694, filed on Jun. 9, 2006.

This application is also a continuation-in-part of U.S. application Ser. No. 11/971,390, filed on Jan. 9, 2008, which is a continuation-in-part of U.S. application Ser. No. 11/363,548, filed on Feb. 27, 2006.

This application is also a continuation-in-part of U.S. application Ser. No. 12/025,414, filed on Feb. 4, 2008, which claims the benefit of U.S. Provisional Application No. 60/953,637, filed on Aug. 2, 2007.

This application claims the benefit of U.S. Provisional Application No. 60/953,620, filed on Aug. 2, 2007.

This application claims the benefit of U.S. Provisional Application No. 60/947,813, filed on Jul. 3, 2007.

This application claims the benefit of U.S. Provisional Application No. 60/911,297, filed on Apr. 12, 2007.

This application claims the benefit of U.S. Provisional Application No. 60/892,349, filed on Mar. 1, 2007.

The disclosures of the above applications are incorporated herein by reference.

INTRODUCTION

Proper alignment of prosthetic components in knee arthroplasty is an important factor in the longevity and function of the implant. Misalignment can cause increased wear of the implant, patient discomfort, and functional limitation.

Although various methods and devices are known for addressing the above problems, patient specific alignment methods and alignment guides are still desirable.

SUMMARY

In one aspect, the present teachings provide an orthopedic apparatus including a patient-specific alignment guide attachable to a surface of a bone being prepared for receiving a prosthetic implant. The alignment guide can include at least first and second components, the first component having a first three-dimensional bone engagement surface and the second component having a second three-dimensional bone engagement surface. The first and second bone engagement surfaces can anatomically match corresponding first and second portions of the surface of the bone. At least one of the first and second components can define at least one alignment formation. The alignment formation can define a guiding bore. The device includes a coupling mechanism connecting the first and second components to one another. The coupling mechanism can be a snap-fit or interlocking mechanism allowing complete separation of the first and second components. The coupling mechanism can alternatively be a hinge allowing relative rotation between the first and second components.

In another aspect, the patient-specific alignment guide can include a first component, a second component and a coupling mechanism interconnecting the first and second components. The first component can have a first surface that is custom designed to conform to a patient's first anatomical portion in three dimensions and having an alignment formation referencing a first axis. The second component can be coupled to the first component and can have a second surface designed to conform to a second anatomical portion of the patient to secure the first surface to the first anatomical portion and having an alignment formation referencing a second axis.

The present teachings also provide a patient positioner that includes a first outer surface shaped to support a portion of a patient's anatomy in a location and orientation determined for image scanning of the portion of the patient's anatomy, and at least one marker visible in image scanning, the image marker integrated with the positioner.

The present teachings provide an orthopedic apparatus that includes a patient-specific alignment guide, and an adjustment mechanism coupled to the alignment guide, the adjustment mechanism providing intra-operative rotational and translational adjustments for a drill guide.

The present teachings provide a method for balancing soft tissue in knee surgery. The method includes attaching a patient-specific alignment guide to a joint surface, tensioning the soft tissue in flexion and/or extension, and balancing the soft tissue relative to the patient-specific alignment guide. Intra-operatively determining the center of the femoral head and balancing relative to the mechanical axis are excluded from the method.

The present teachings also provide a manufacturing assemblage that includes a first patient specific alignment guide, a second patient specific alignment guide, and a connection arm coupled to the first alignment guide at a first connection end and to the second alignment guide at a second connection end. The connection arm retains together the first and second alignment guides, and includes frangible features.

Further areas of applicability of the present invention will become apparent from the description provided hereinafter. It should be understood that the description and specific examples are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 11A is a perspective view of the femoral alignment guide of FIG. 8 shown with a drill guide;

FIG. 11B is a perspective view of the femoral alignment guide of FIG. 11A shown with two guide pins drilled through the drill guide;

FIG. 11C is perspective view of the femoral alignment guide of FIG. 11B showing the removal of the drill guide;

FIG. 17 is an environmental view illustrating a patient positioner according to the present teachings;

FIG. 18 is an environmental view of a patient-specific guide according to the present teachings;

FIG. 19 is an environmental view of a patient-specific guide according to the present teachings.

FIG. 22A is an environmental view of an exemplary alignment guide according to the present teachings shown on a joint surface assembled with a drill guide;

FIG. 22B is a partially cutout detail of a perspective view of an exemplary alignment guide according to the present teachings shown on a joint surface assembled with a drill guide;

FIG. 23A is a perspective view of the drill guide of FIG. 3B shown in a first configuration;

FIG. 23B is a perspective view of the drill guide of FIG. 23A shown in a second configuration;

FIG. 23C is a perspective view of the drill guide of FIG. 23B shown in a third configuration;

DESCRIPTION OF VARIOUS ASPECTS

The following description is merely exemplary in nature and is in no way intended to limit the scope of the present teachings, applications, or uses. For example, although the present teachings are illustrated for alignment guides in knee surgery, the present teachings can be used for other guides, templates, jigs, drills, rasps or other instruments used in various orthopedic procedures.

The present teachings provide a method for preparing patient-specific alignment guides for use in orthopedic surgery for a joint, such as, for example, the knee joint. Conventional, not patient-specific, prosthesis components available in different sizes can be used with the alignment guides, although patient-specific femoral and tibial prosthesis components prepared with computer-assisted image methods can also be used. Computer modeling for obtaining three dimensional images of the patient's anatomy, such as a patient's joint, for example, the patient-specific prosthesis components, when used, and the alignment guides and templates can be provided by various CAD programs and/or software available from various vendors or developers, such as, for example, from Materialise USA, Ann Arbor, Mich.

Figure 1:
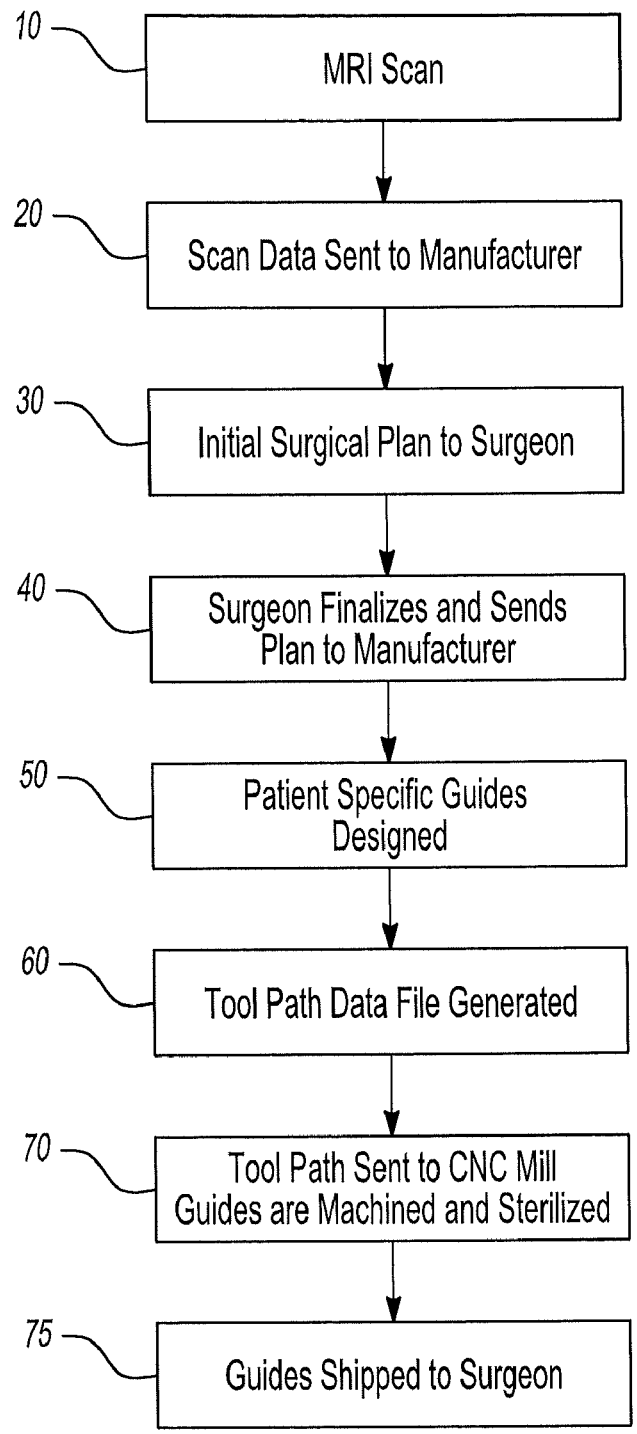
FIG. 1 is a flowchart of an exemplary method of preparing patient specific alignment guides according to the present teachings.
Figure 2:
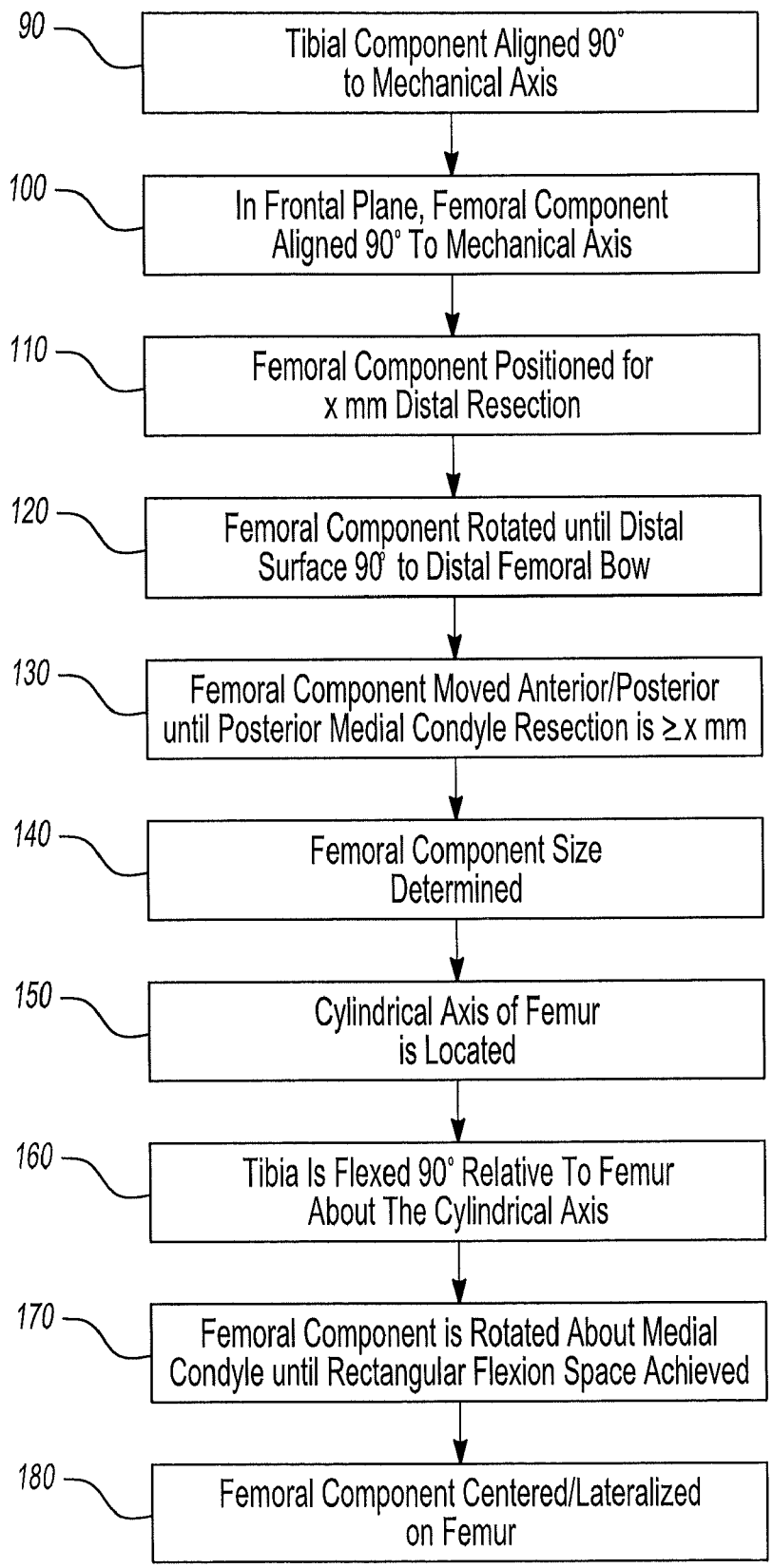
FIG. 2 is a flowchart of an alignment method according to the present teachings.
Figure 3:
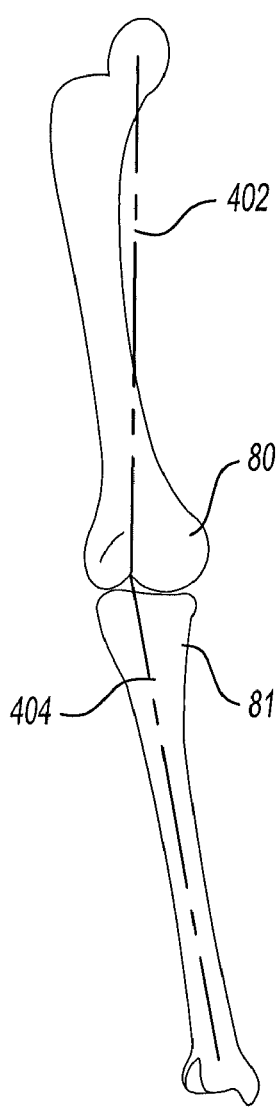
FIG. 3 is a view illustrating the mechanical axis in a patient's anatomic image.

Referring to FIG. 1, an MRI scan or a series of CT scans of the entire leg of the joint to be reconstructed, including hip and ankle, as shown in FIG. 3, can be performed at a medical facility or doctor's office, at aspect 10. In some cases, the scan may be performed with the patient wearing an unloader brace to stress the ligaments. The scan data obtained can be sent to a manufacturer, at aspect 20. The scan data can be used to construct a three-dimensional image of the joint and provide an initial implant fitting and alignment in a computer file form or other computer representation. The initial implant fitting and alignment can be obtained using an alignment method, such as the alignment method illustrated in FIG. 2 and described below. Other alignment methods can also be used, such as alignment protocols used by individual surgeons.

As discussed above, in the preoperative planning stage of a surgical procedure, multiple image scans of portions of the patient's anatomy related to the procedure are obtained. The patient's anatomy is placed on a positioner for obtaining the appropriate location and orientation for imaging. Patient positioners are available in various shapes and sizes appropriate for the particular portion of the anatomy that needs to be supported in a specific orientation. Several scans can be obtained. Conventionally, image marker visible in the MRI scan can be placed on the patient's anatomy to allow image scaling and orientation. The obtained scans of the desired anatomy can be correlated to one another to reconstruct an image of the patient's specific anatomy in three-dimensions.

The present teachings provide a patient positioner that includes image markers and eliminates the need to place image markers on the patient.

Referring to FIG. 17, an exemplary positioner 800 is illustrated in connection with imaging of a patient's knee 83. The positioner 800 has a first outer surface 802 which is shaped to position and orient at least a portion of the patient's leg and the knee 83 in a particular configuration. It will be appreciated that for imaging of other joints or portions of the patient's anatomy, the first surface 802 is configured to conform and support the corresponding portions of the patient. The positioner 800 can be made of appropriate materials for providing support and can include cushioning at least over the first surface 802 that comes in contact with the patient. The positioner 800 can also be made of materials that are MRI or image invisible, either in whole or in part, such as on the portions that are in proximity of the patient's anatomy to avoid interference with imaging.

The positioner 800 can include one or more image markers 804 that are MRI or image visible, such that the markers are visible in the images of the patient's anatomy and assist in identification and image orientation. When multiple image scans of large portions of the patient's anatomy are obtained, the markers 804 can be used to combine the multiple scans in an integrated image of a larger portion of the anatomy. Placing the image markers 804 on the positioner 800 rather than on the patient can provide better accuracy and consistency for imaging, and can also simplify the patient preparation procedure. The image markers 804 can be placed on a second outer surface 808 of the positioner 800 or can be embedded in the interior 810 of the positioner.

The positioner 800 can include one or more fasteners 806, such as straps or other devices for holding the patient's leg or other anatomy portion in the desired position for imaging.

Figure 7:
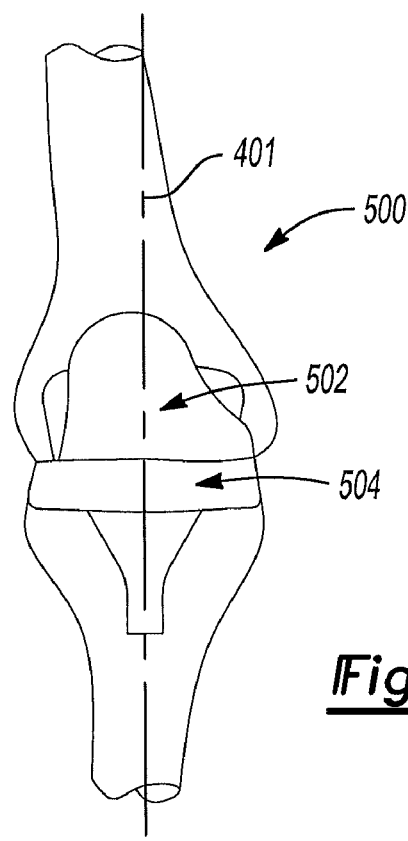
FIG. 7 is an exemplary image of a patient's anatomy with implants shown, as viewed in interactive software according to the present teachings.
Figure 8:
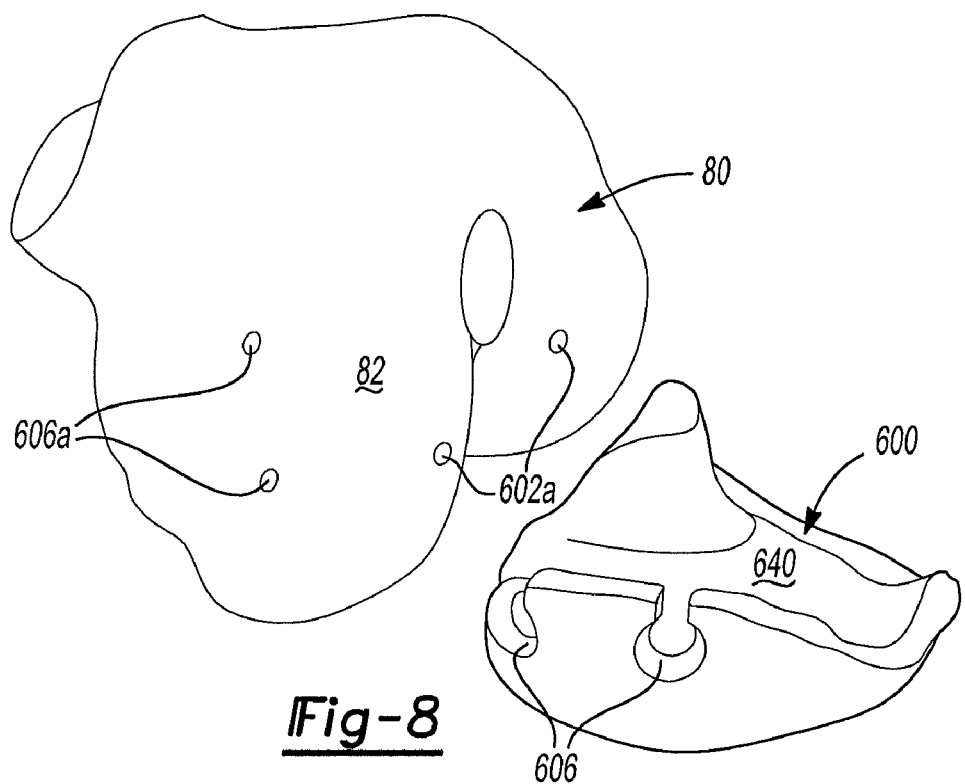
FIG. 8 is a perspective view of an exemplary femoral alignment guide according to the present teachings, shown next to a corresponding anatomic femur.

The outcome of the initial fitting is an initial surgical plan that can be printed or provided in electronic form with corresponding viewing software. The initial surgical plan can be surgeon-specific, when using surgeon-specific alignment protocols. The initial surgical plan, in a computer file form associated with interactive software, can be sent to the surgeon, or other medical practitioner, for review, at 30. The surgeon can incrementally manipulate the position of images of implant components 502, 504 in an interactive image form 500 of the joint, as illustrated in FIG. 7. After the surgeon modifies and/or approves the surgical plan, the surgeon can send the final, approved plan to the manufacturer, at 40.

Various methods of sending the initial and final surgeon-approved surgical plans can be used. The surgical plans can be, for example, transferred to an electronic storage medium, such as CD, DVD, flash memory, which can then be mailed using regular posting methods. Alternatively, the surgical plan can be e-mailed in electronic form or transmitted through the internet or other web-based service, without the use of a storage medium.

After the surgical plan is approved by the surgeon, patient-specific alignment guides for the femur and tibia can be developed using a CAD program or other imaging software, such as the software provided by Materialise, for example, according to the surgical plan, at 50. Computer instructions of tool paths for machining the patient-specific alignment guides can be generated and stored in a tool path data file, at 60. The tool path can be provided as input to a CNC mill or other automated machining system, and the alignment guides can be machined from polymer, ceramic, metal or other suitable material, and sterilized, at 70. The sterilized alignment guides can be shipped to the surgeon or medical facility, at 75 for use during the surgical procedure.

Figure 4:
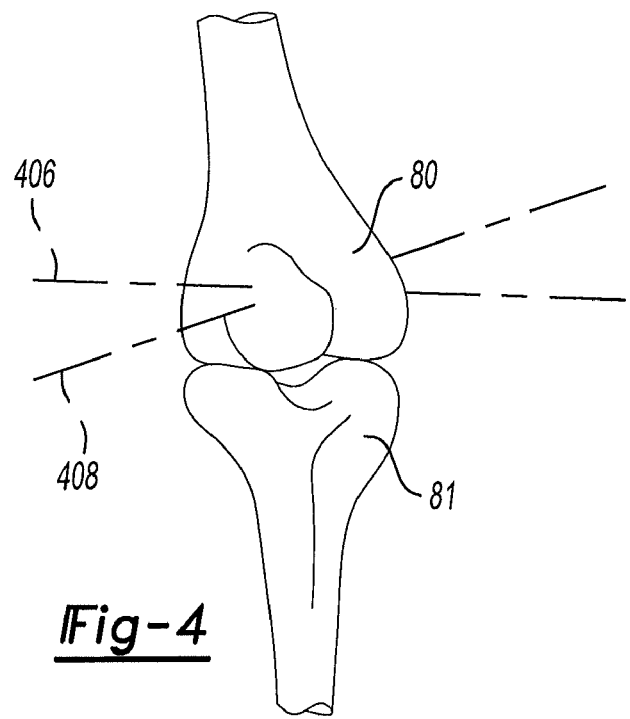
FIG. 4 is a view illustrating the transepicondylar and cylindrical axes in a patient's anatomic image.

Referring to FIG. 2, an exemplary method for providing the initial implant fitting and alignment is illustrated. The method can be modified or completely replaced according to a surgeon-specific alignment protocol. After the scan data is converted to three dimensional images of the patient anatomy from hip to ankle, images of the tibial and femoral components can be manipulated for obtaining patient-specific alignment by making use of the femoral and tibial mechanical axes 402, 404, illustrated in FIG. 3, and the transepicondylar and cylindrical axes 406, 408, illustrated in FIG. 4. Images of the knee joint anatomy can include images of the joint surfaces of the distal femur and proximal tibial with or without the associated soft tissues, such as articular cartilage, on the respective bone surfaces.

Generally, the femoral mechanical axis is defined as the line joining the center of the femoral head and the center of the intercondylar notch. The femoral anatomic axis is defined as the line along the center of the femoral shaft. The tibial mechanical axis is the line joining the center of the tibial plateau to the center of the tibial plafond or the center of the distal end of the tibia. The tibial anatomic axis is the line along the center of the tibial shaft. The transepicondylar axis is the line connecting the most prominent points of the epicondyles. The cylindrical axis is the line connecting the centers of the condyles when the condyles are approximated by coaxial cylinders. A detailed discussion of the various joint-related axes and the relation of the transepicondylar axis 406 and cylindrical axis 408 is provided in Eckhoff et al, *Three-Dimensional Mechanics, Kinematics, and Morphology of the Knee Viewed in Virtual Reality*, J Bone Joint Surg Am. 87:71-80, 2005, which is incorporated herein by reference.

Figure 5:
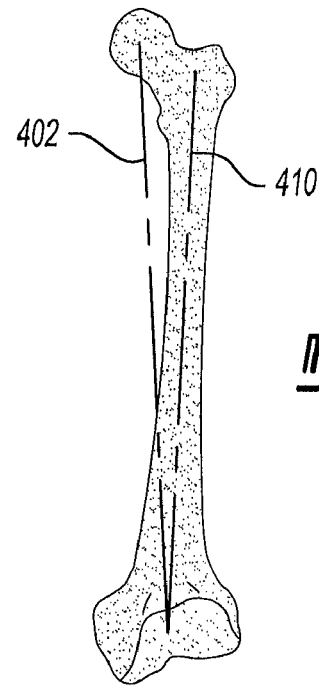
FIG. 5 is a view illustrating the mechanical and anatomic axes in a patient's femoral image.

The relation of the femoral mechanical axis 402 to the anatomic axis 410 for the femur is illustrated in FIG. 5. The femoral and tibial mechanical axes 402, 404 may or may not coincide, as illustrated in FIG. 3. In the following discussion, reference is made to a single mechanical axis 401 encompassing the femoral and tibial mechanical axes 402, 404. The alignment procedure illustrated in FIG. 2 makes use of the mechanical, anatomic, transepicondylar and cylindrical axes in various degrees. The present teachings, however, are not limited to this alignment procedure. Multiple alignment procedures can be provided to accommodate the experience and preference of individual surgeons. For example, the alignment procedure can be based on the anatomic and mechanical axes, or can be substantially based on the cylindrical axis. Further, the alignment procedure can be deformity-specific, such that is adapted, for example, to a valgus or varus deformity.

With continued reference to FIGS. 2-5 and 7, in the image space, the tibial component 504 can be aligned 90° to the mechanical axis 401, at aspect 90. In the frontal plane, the femoral component 502 can be aligned 90° to the mechanical axis 401, at aspect 100. The femoral component 502 can be positioned for "x" mm distal resection, at 110, where "x" can be about 9 mm or as other measurement as indicated for a specific patient. The femoral component 502 can be rotated until its distal surfaces are at 90° to the distal femoral bow (component flexion/extension), at 120. The femoral component 502 can be moved anteriorly/posteriorly until the posterior medial condyle resection is greater or equal to "x" mm, at aspect 130.

The femoral component size can be determined by observing the anterior resection relative to anterior cortex, at 140. If the femoral size is adjusted, the new size can be positioned at the same location relative to the distal and posterior cut planes.

The cylindrical axis 408 of the femur can be located, at aspect 150. The tibia can be flexed 90° relative to the femur about the cylindrical axis 408, at aspect 160. The femoral component 502 can be rotated about the medial condyle until a rectangular flexion space is achieved, at aspect 170. Alternatively, the rotation can be relative to the transepicondylar axis, anterior/posterior axis, and posterior condylar axis, or a combination of all four axes. The femoral component 502 can be centered or lateralized on the femur, at aspect 180. The location for various distal holes for locating the femoral resection block can be also determined.

Referring to FIGS. 6, and 8-15B, an exemplary alignment guide 600 and method of use is illustrated in connection with the patient's femur 80. Reference numbers 200-250 relate to aspects of the method of FIG. 6 and are described in connection with the instruments shown in FIGS. 8-15B for the femur 80.

The alignment guide 600 includes an inner guide surface 640 designed to closely conform, mate and match the femoral joint surface 82 of the patient in three-dimensional space such that the alignment guide 600 and the femoral joint surface are in a nesting relationship to one another. Accordingly, the alignment guide 600 can conform, mate and snap on or "lock" onto the distal surface of the femur 80 in a unique position determined in the final surgical plan, at 200. The alignment guide 600 can have variable thickness. In general, the alignment guide 600 can be made as thin as possible while maintaining structural stiffness. For example, certain areas around and adjacent various securing or guiding apertures 602, 606 can be thickened to provide structural support for guiding a drill or for holding a drill guide or supporting other tools or devices. Exemplary thickened areas 642 are indicated with dotted lines in FIGS. 9A and 9B. Other areas can be cut out for viewing the underlying bone or cartilage of femoral joint surface 82. Viewing areas 644 are indicated with dotted lines in FIGS. 9A and 9B.

Figure 9A:
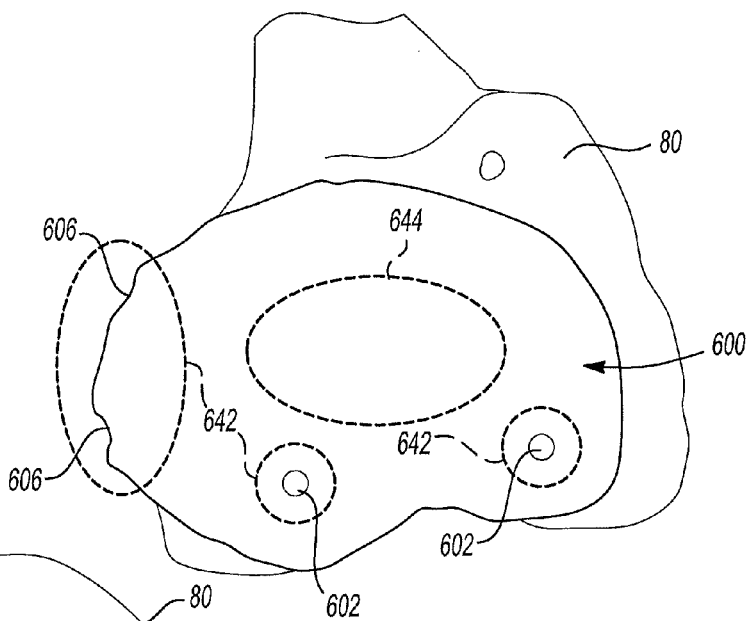
FIGS. 9A and 9B are perspective view of the femoral alignment guide of FIG. 8 shown mounted on the femur.
Figure 9B:
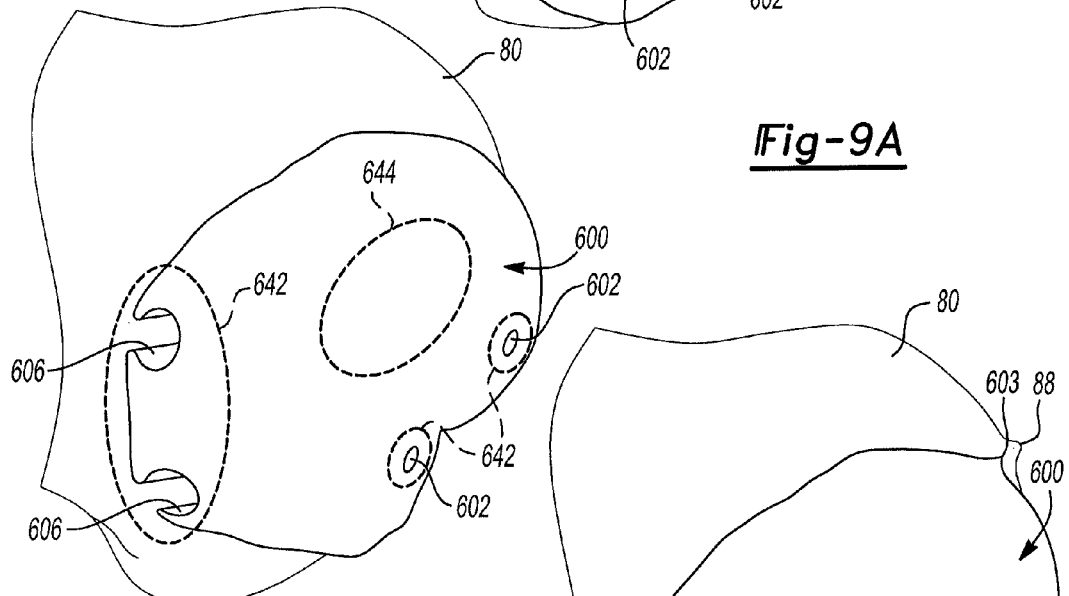
Figure 9C:
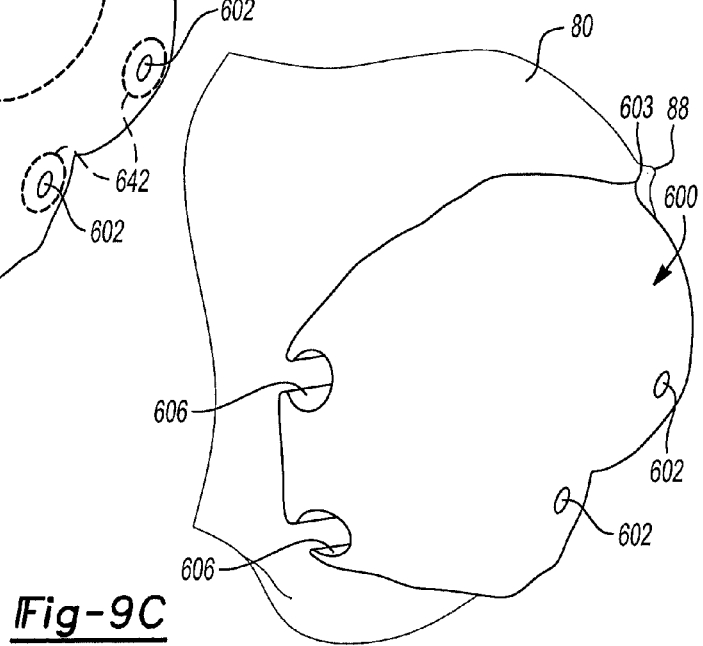
FIG. 9C is an environmental perspective view of alignment guide according to the present teachings, the alignment guide shown mounted on a femur.

Referring to FIG. 9C, the alignment guide 600 can have an indicator feature 603 pointing to a prominent landmark 88, such as an osteophyte or other anatomic feature on the femur 80. The indicator feature 603 can be, for example, a pointed protrusion, a groove or other physical or visual mark that is to associated with the landmark 88 to provide a visual indication that the alignment guide is correctly positioned on the femur 80.

Figure 10A:
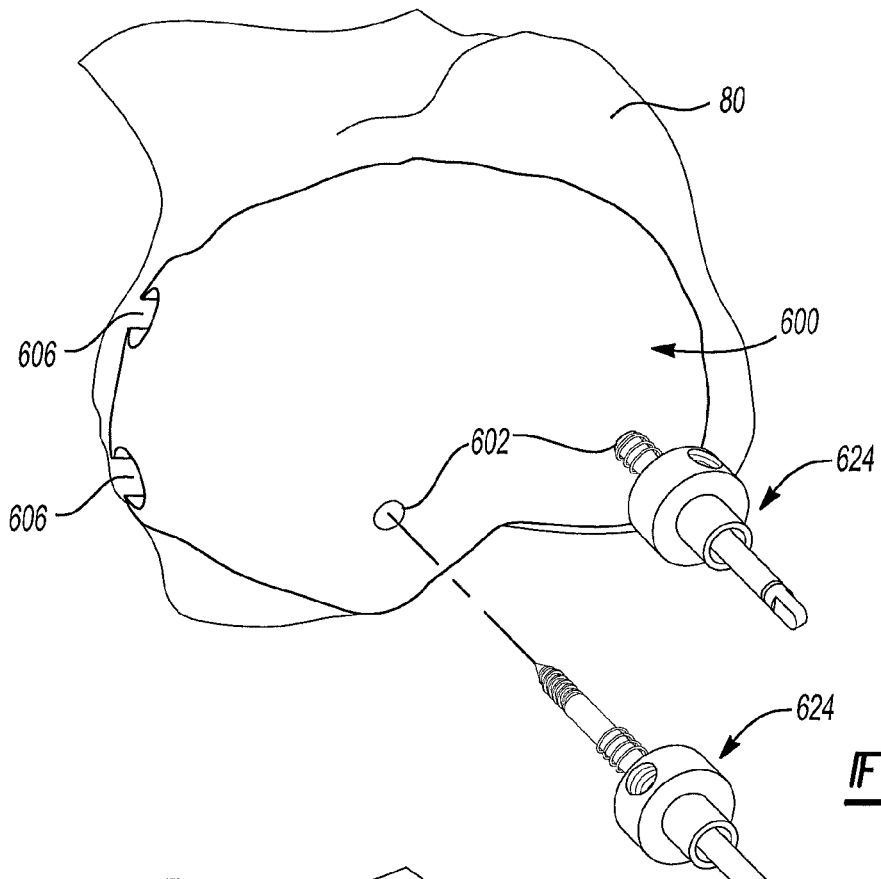
FIGS. 10A and 10B are perspective view of the femoral alignment guide of FIG. 8 shown with spring pins securing the alignment guide to the femur.
Figure 10B:
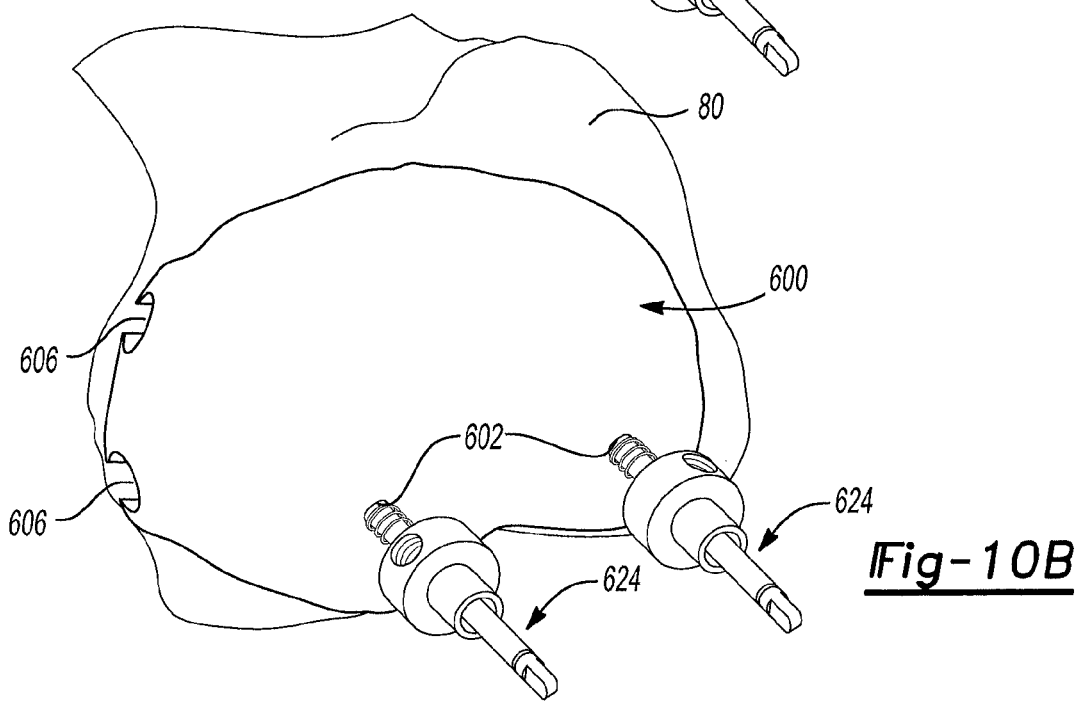
Figure 13A:
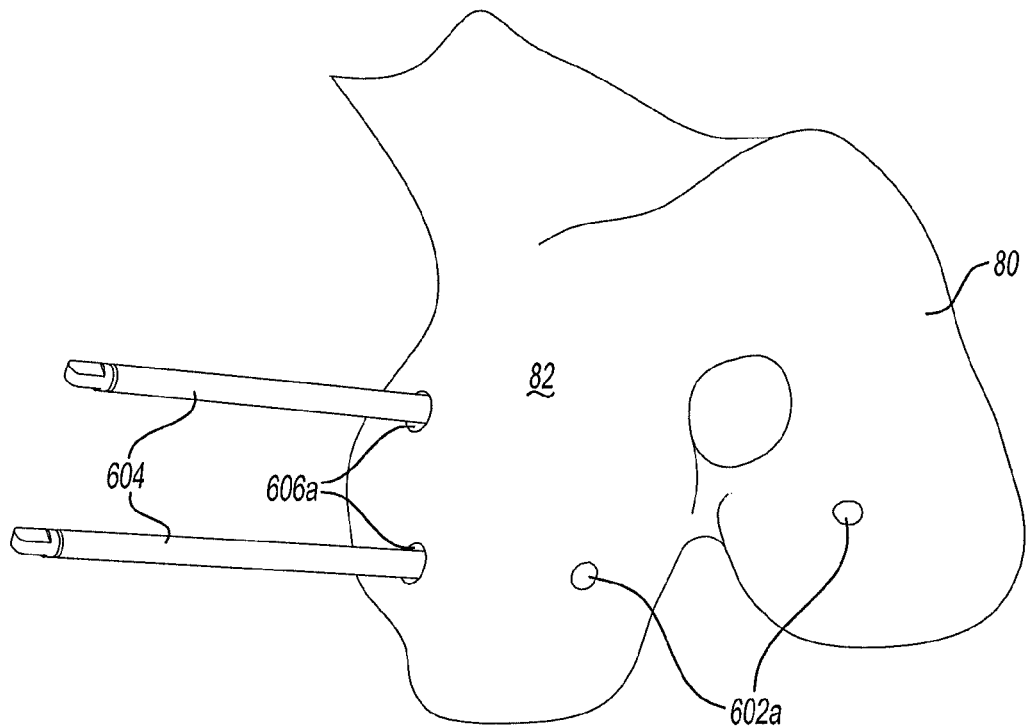
FIG. 13A is a perspective view of FIG. 12B illustrating the guide pins after the removal of the femoral alignment guide.
Figure 13B:
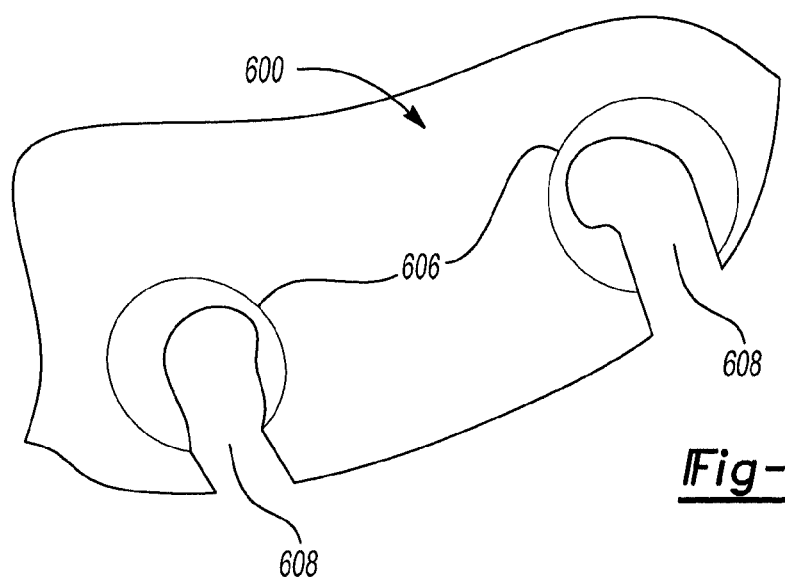
FIG. 13B illustrated a detail of the femoral alignment guide of FIG. 12B.

Referring to FIGS. 10A and 10B, the alignment guide 600 can be secured to the femoral joint surface 82 with fixation members or fasteners 624, such as, for example, spring pins, or other securing fasteners that are received through distal apertures 602 of the alignment guide 600. Locating holes 602a corresponding to the apertures 602 of the alignment guide 600 can be drilled in the distal femur 80 to locate a femoral resection block or other cutting device 620, such as a 4-in-1 cutting block, at 220. The alignment guide 600 can also include guiding apertures 606. Guiding apertures 606 are shown in the anterior-medial side relative to the femur 80, but can also be made in the anterior side of the femur 80 or in other locations and orientations. The guiding apertures 606 can be counter-bored and have a partially open portion 608 in their perimeter for sliding the alignment guide off pins or other fasteners without removing such fasteners, as shown in FIG. 13A and discussed below.

Referring to FIGS. 11A and 11B, a drill guide 700 can be placed in alignment with the guiding apertures 606. The drill guide 700 can include a body 702 having guiding bores 704 corresponding to the guiding apertures 606. The guiding bores 704 can have portions 706 that extend beyond the body 702 and into the guiding apertures 606 for facilitating alignment. The drill guide 700 can also include a handle 710 extending sideways from the body 702 and clear from the drilling path.

Figure 6:
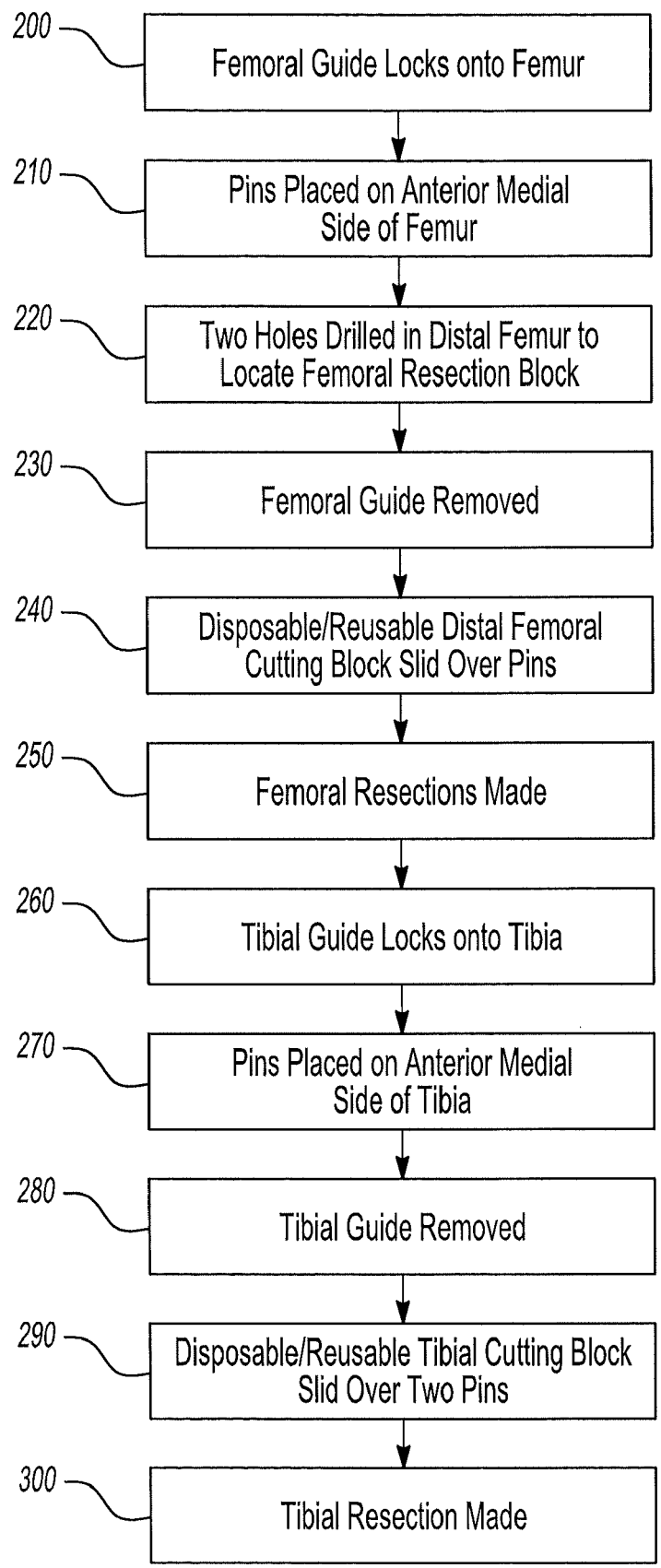
FIG. 6 is a flowchart of an exemplary method of using patient specific alignment guides according to the present teachings.

Referring to FIG. 11C, guide elements 604, such as pins or other fasteners, for example, can be drilled through the guiding bores 704 of the drill guide 700 on the anterior or anterior-medial side of the femur 80, at aspect 210 of the method of FIG. 6. The guide elements 604 can be parallel or at other angles relative to another. The guide elements 604 can define a plane that is parallel to a distal resection plane for the femur.

Figure 12A:
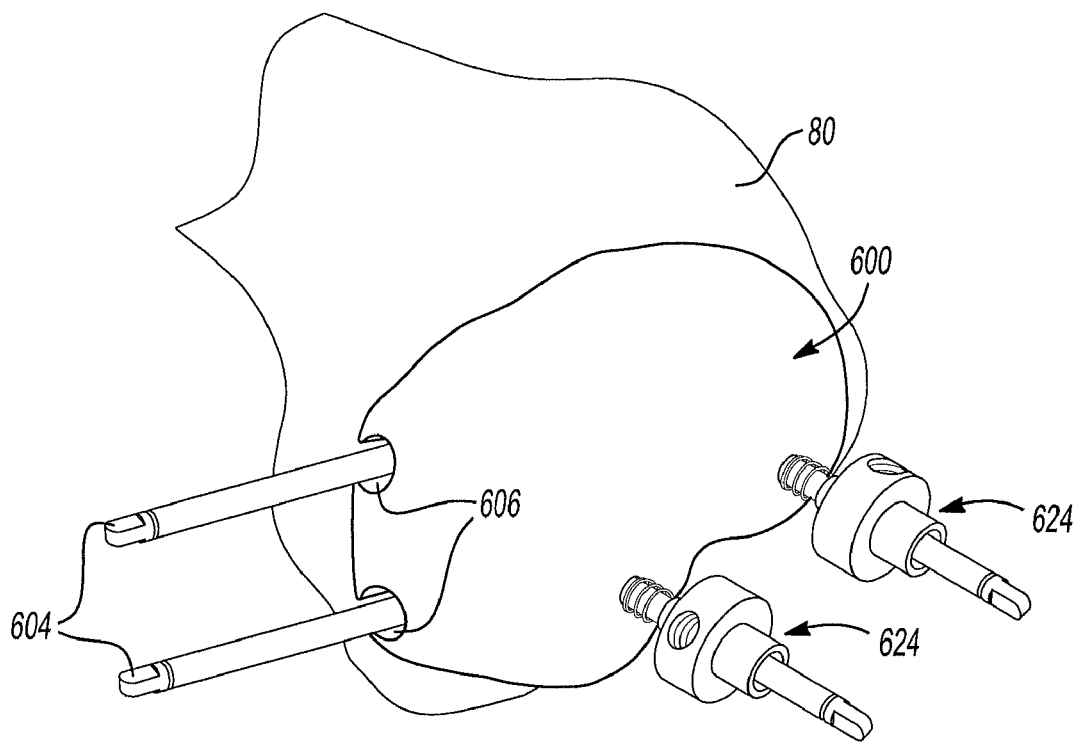
FIG. 12A is a perspective view of the femoral alignment guide of FIG. 11C shown after the removal of the drill guide.
Figure 12B:
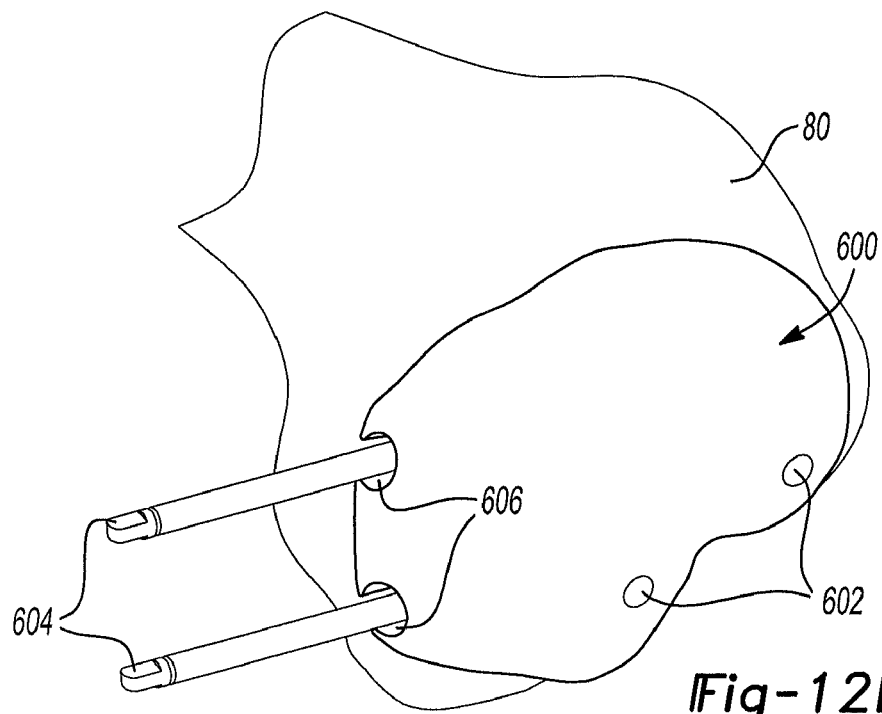
FIG. 12B is a perspective view of the femoral alignment guide of FIG. 12A shown after the removal of the spring pins.

Referring to FIG. 12A, the drill guide 700 can be removed. Referring to FIGS. 12B-13B, the fasteners 624 can be removed, and the alignment guide 600 can be removed from the femur 80 by sliding the alignment guide 600 off the guide elements 604 through the open portions 608 of the guiding apertures 606 without removing the guide elements 604 at the anterior/medial corner of the knee, at aspect 230 of FIG. 6.

The guide elements 604 can be used to prepare the joint surfaces for the prosthesis by mounting cutting guides/blocks for resecting the joint surface. Alternatively, a robotic arm or other automated, guided or computer controlled device that can guide the resections based on the pre-operative surgical plan can be mounted on the guide elements 604 and assist the surgeon in preparing the joint surface for the prosthesis.

Figure 14A:
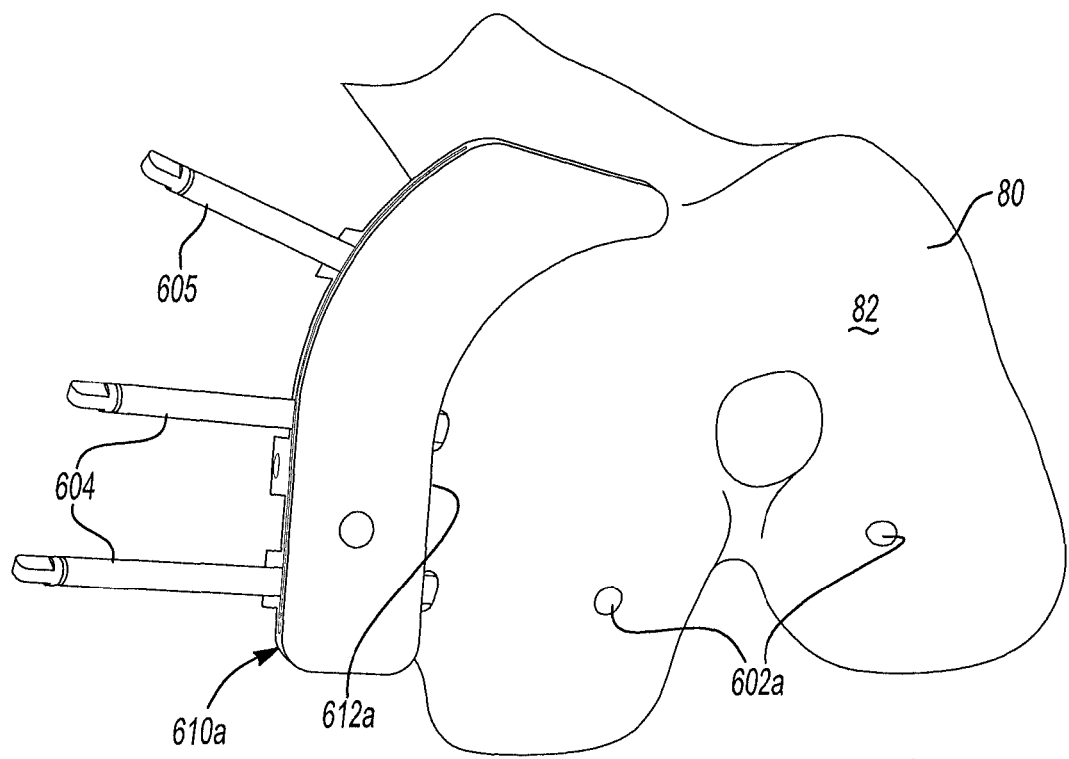
FIG. 14A is a perspective view of distal femoral cutting block shown over two pins on a patient's femur, according to the present teachings.
Figure 14B:
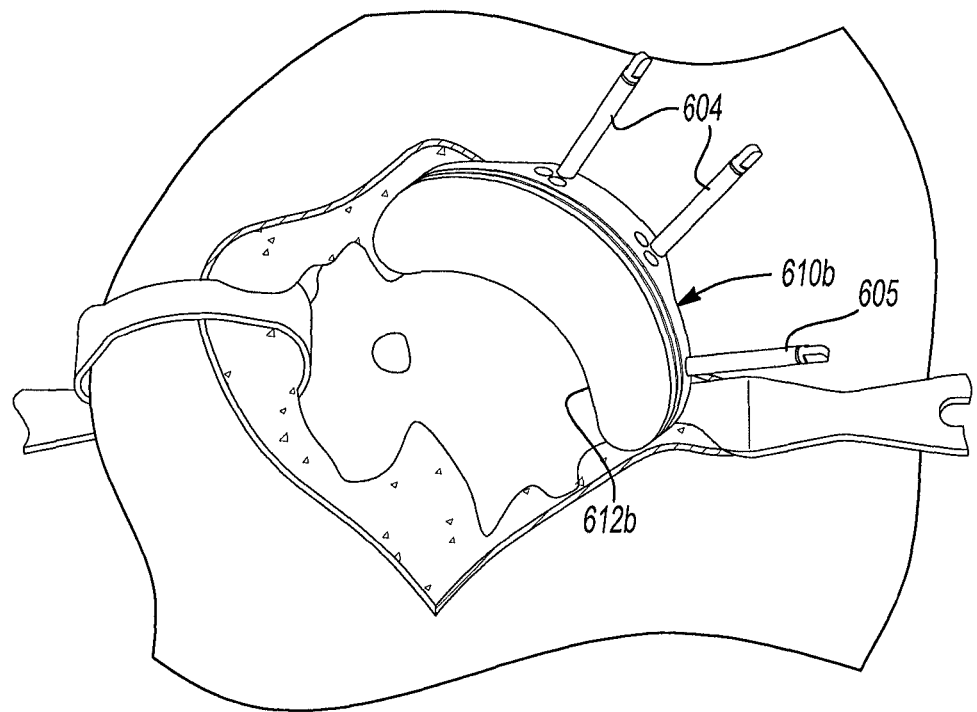
FIG. 14B is a perspective view of distal femoral cutting block shown over two guide pins on a patient's femur, according to the present teachings.

Referring to FIGS. 14A and 14B, exemplary distal cutting blocks 610a, 610b that can be mounted over the guide element 604 for making the distal resection, at aspect 640 of FIG. 6, are illustrated. A third fixation element 605, obliquely oriented relative to the guide elements 604 can also be used. The distal cutting blocks 610a, 610b can have an inner surface 612a, 612b that generally follows the shape of the femur 80 to a lesser or greater degree. The distal cutting blocks 610a, 610b can be disposable or re-usable.

Figure 15A:
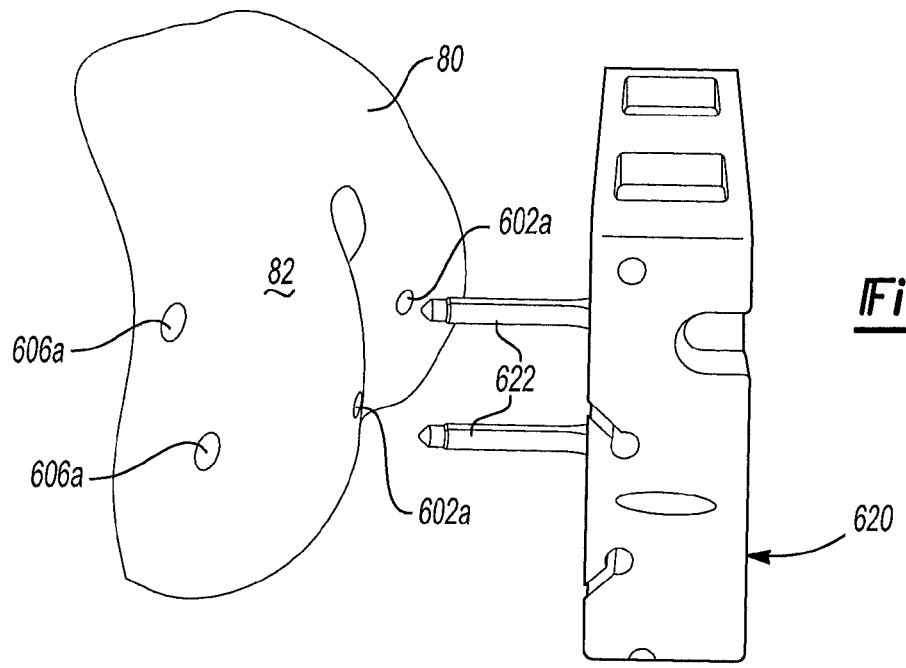
FIG. 15A is a perspective view of an exemplary 4-in-1 cutting block positioned on the femur with reference to holes corresponding to the spring pins.
Figure 15B:
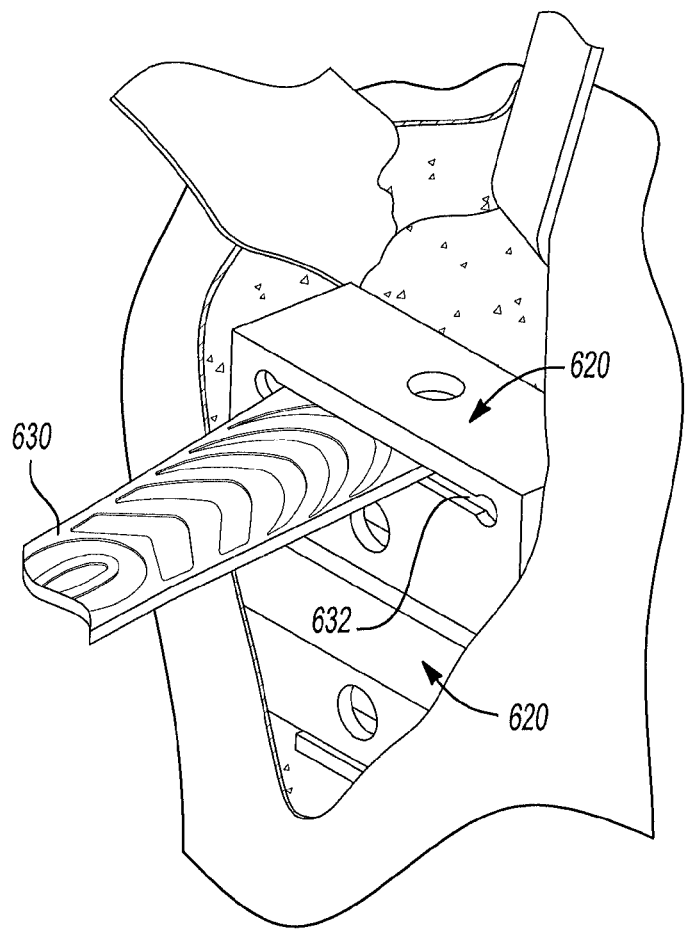
FIG. 15B a perspective view of the cutting block of FIG. 15A shown with a cutting blade.

Referring to FIGS. 15A and 15B, after the distal resections are made with the distal cutting block 610a or 610b, the femoral resection block 620 can be mounted with pegs or other supporting elements 622 into the holes 602a corresponding to the fasteners 624. The femoral resections can be made using, for example, a cutting blade 630 through slots 632 of the femoral resection block 620, at aspect 250 of FIG. 6.

Referring to FIGS. 6 and 16A-D, an exemplary alignment guide 600 is illustrated in connection with the patient's tibia 81. Reference numbers 260-300 relate to aspects of the method of FIG. 6 and are described in connection with the instruments shown in FIGS. 16A-16D for the tibia.

Figure 16A:
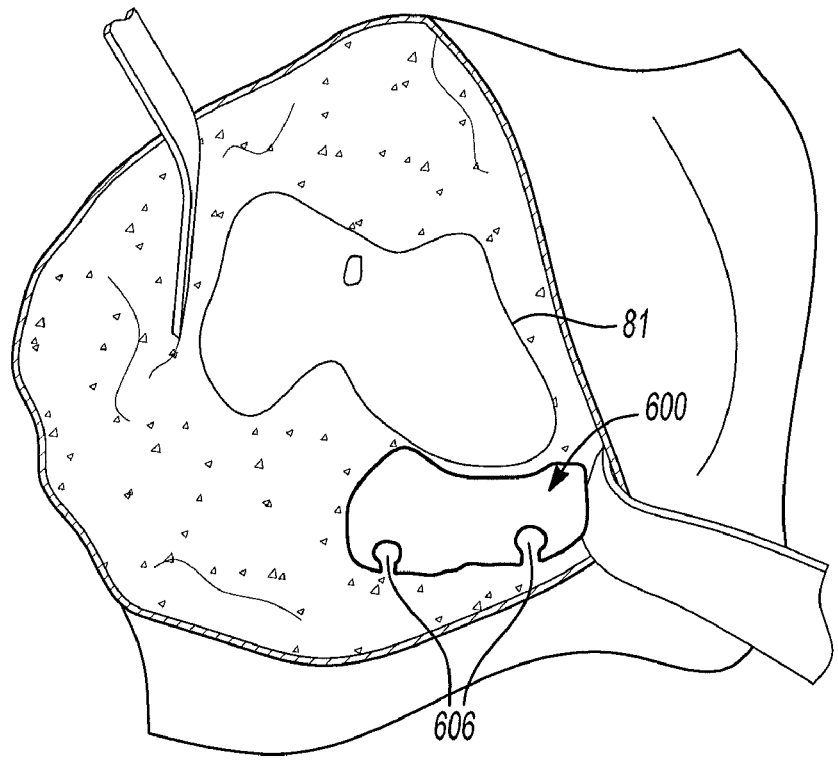
FIG. 16A is a perspective view of a tibial alignment guide according to the present teachings, shown mounted on the tibia.
Figure 16B:
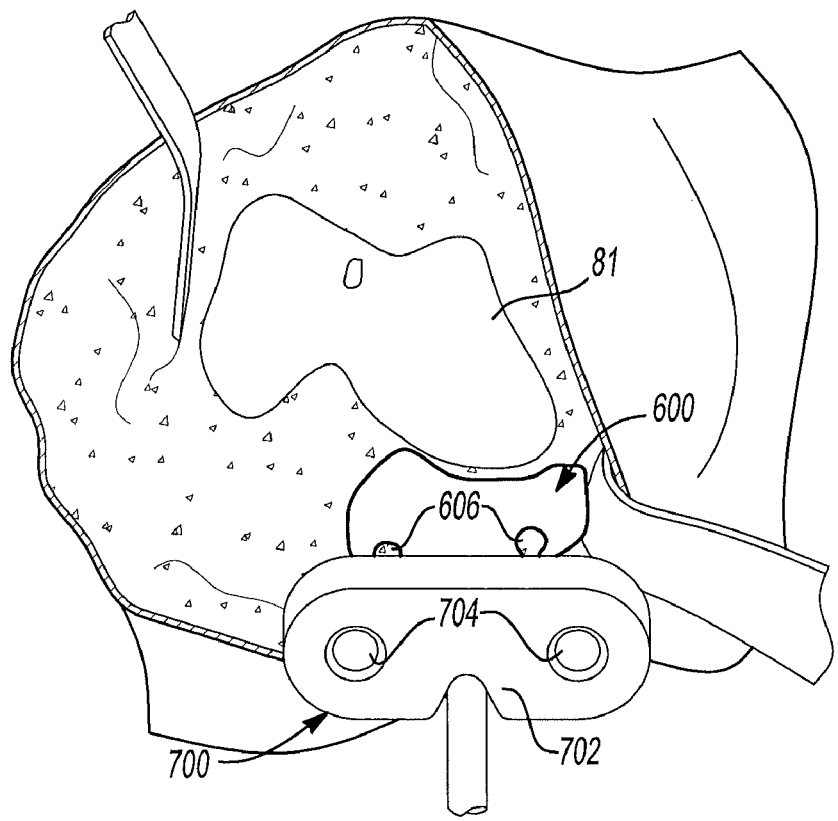
FIG. 16B is a perspective view of the tibial alignment guide of FIG. 16A shown with a drill guide.
Figure 16C:
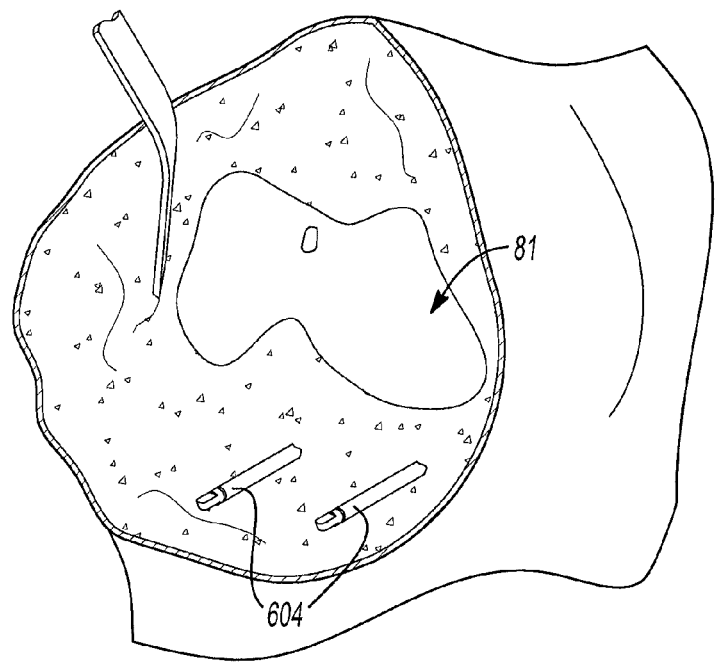
FIG. 16C is a perspective view of FIG. 16B illustrating the guide pins after the removal of the tibial alignment guide.
Figure 16D:
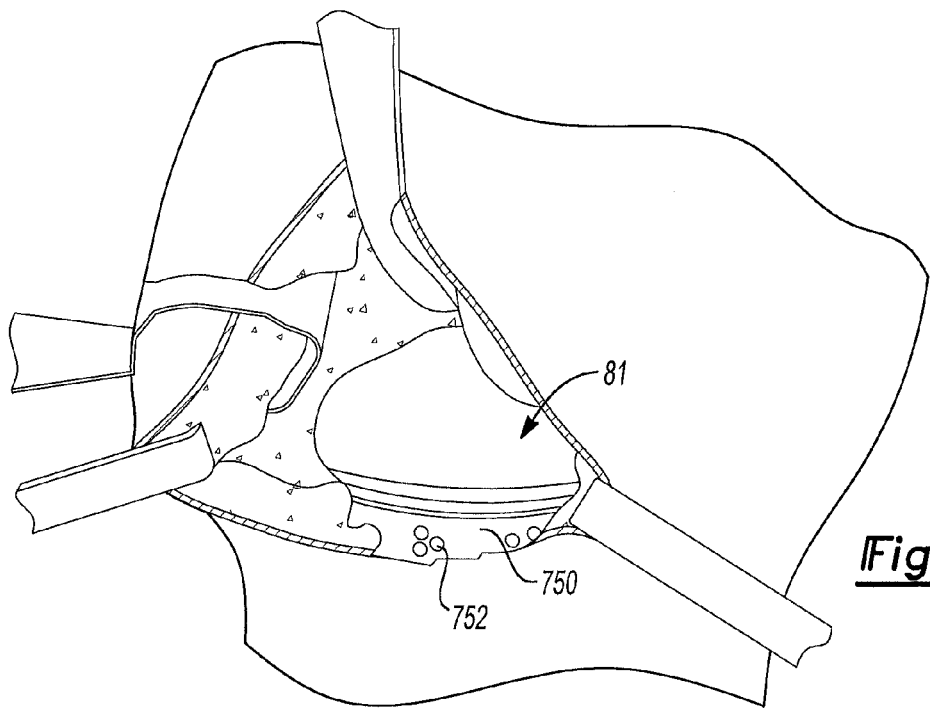
FIG. 16D is a perspective view of FIG. 16C illustrating a tibial cutting guide mounted on the guide pins.

The alignment guide 600 can conform, nestingly mate in three-dimensional space and snap on or "lock" by design onto the tibia 81 in a unique position, at aspect 260 of FIG. 6. The alignment guide 600 can wrap around the anterior-medial edge of the tibia 81, as shown in FIG. 16A. The drill guide 700 can be aligned with the counter-bored guiding apertures 606 of the alignment guide 600, as shown in FIG. 16B. Two or more guide elements 604 can be placed on the anterior medial side of the tibia, at aspect 270 of FIG. 6. An additional fixation element can also be used for additional securing for the alignment guide 600. The drill guide 700 and the alignment guide 600 can be removed, leaving behind the guide elements 604 attached, at aspect 280 of FIG. 6, and as shown in FIG. 16C. A disposable or reusable tibial cutting block 750 can be slid over the guide elements 604, at aspect 290 of FIG. 6, and as shown in FIG. 16D. The tibial cutting block 750 can include a series of holes 752, allowing the cutting block 750 to be translated proximally or distally to adjust the level of the distal resection. The tibial resection can be made, at 300.

The present teachings provide patient-specific alignment guides that can be used for alignment in orthopedic surgery.

Each alignment guide includes an inner surface that nestingly mates and conforms in three-dimensional space with a corresponding joint surface of a specific patient. The alignment guides can be used for locating guide elements on the joint surface. After the alignment guides are removed, cutting guides or other cutting devices, including automated or robotic devices, can be mounted on the guide elements for making various resection cuts. Because the alignment guides are not used for cutting, the alignment guides do not require substantive thickness to extend anteriorly, and consequently have a lower profile, and less weight. Additionally, because the alignment guides are removed before cutting, the present teachings provide increased ability to visualize the cuts and the cutting process.

Figure 20:
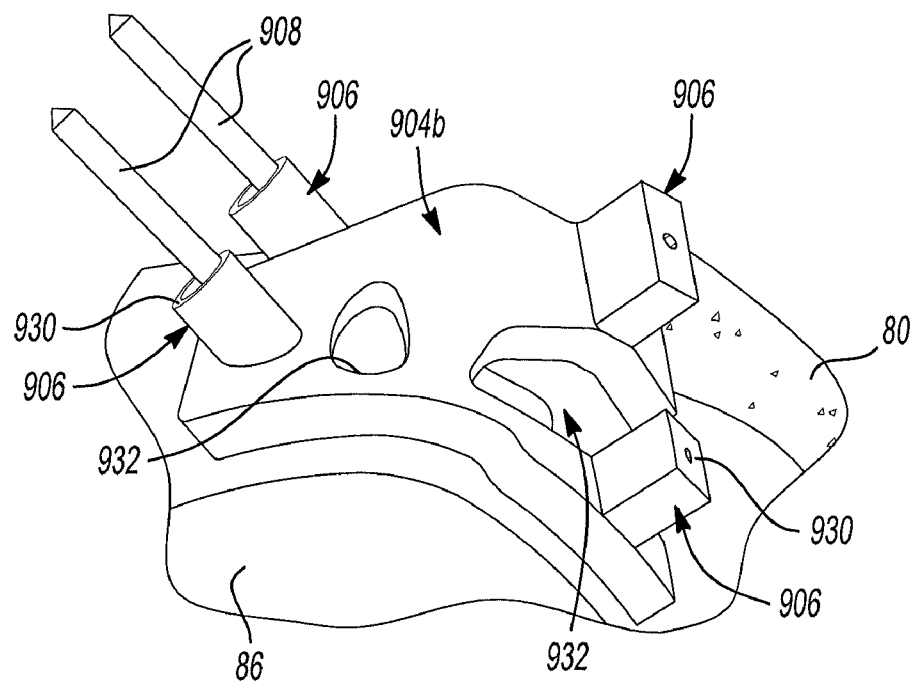
FIG. 20 is an environmental view of a patient-specific guide according to the present teachings.

Referring to FIGS. 18-20, two exemplary multiple-component implant guides 900a, 900b (collectively referenced with character 900) are illustrated. In these exemplary embodiments, the implant guide 900 is shown with first and second adjacent components 902 and 904, although more than two components can be similarly included in the implant guide 900. The first and second components 902, 904 can be movably and/or removably connected to one another with a coupling mechanism 920. The coupling mechanism 920 can be selected from a variety of mechanisms that provide easy intra-operative assembly. In one aspect, for example, the coupling mechanism 920 can be a snap-fit connection between the two components. In another aspect, the coupling mechanism 920 can be an interlocking mechanism, such as a key-and-tab mechanism, a dovetail mechanism, a jig-jaw puzzle interlocking mechanism, or any other interlocking mechanism. In another aspect, the coupling mechanism 920 can include a permanent or temporary hinge or other pivotable structure that allows relative motion between the adjacent components, such that one component can be rotated relative to the other component for ease of positioning on the patient. The components can be permanently pivotably coupled with the hinge or can be detachable.

Referring to FIG. 18, the exemplary implant guide 900a can be configured for the femoral neck 84 of a proximal femur 85. The implant guide 900a, when assembled, can wrap around the femoral neck 84 for assisting in the placement of an alignment pin 908 for femoral resurfacing. The first component 902a can include a guiding portion or formation 906 and a portion 912 having a first three-dimensional inner bone engagement surface 913 that can anatomically match or mate with a portion of the femoral neck 84 in three dimensions. The guiding formation 906 can include a guiding bore, a hole, or other opening through which an alignment pin 908 or drill bit or other supporting device can be inserted. The second component 904a can be coupled to the first component 902a by the coupling mechanism 920a. The second component 904a include a second three-dimensional inner bone engagement surface 905 that can anatomically match and mate with substantially the remaining portion of the femoral neck 84 in three dimensions, without requiring other supports to retain the guide 900a on the proximal femur 85. It will be appreciated that such arrangement would not be possible with a single-component implant guide.

Referring to FIGS. 19 and 20, the exemplary implant guide 900b can be configured for encasing an osteophyte 86 or other bone growth that may be associated with osteoarthritis or other bone malformation of the distal femur 80. The first component 902b can include a first inner bone engagement surface 907 adapted to anatomically match and conform on the osteophyte 86 in three dimensions. The second component 904b can interlock with the first component 902b with the coupling mechanism 920b, and can have a second inner bone engagement surface 921 that can anatomically match or mate with another portion of the distal femur 80 in three dimensions. The second component 904b can include one or more guiding formations 906, such as, for example, cylindrical or rectangular blocks having alignment bores 930 for guiding alignment or support pins 908, drill bits, cutting blocks or other instruments and devices, including prosthetic devices. The pins 908 can be used to support the second component 904b on the distal femur 80. The first component 902b can be supported on the distal femur 80 by being connected with the second component 904b with the coupling mechanism 920b, which can be a snap-fit coupling, interlock coupling or a hinge, as discussed above. The second component 904 can include one or more viewing windows 932, as shown in FIG. 20.

It will be appreciated that other multiple-component guides can be similarly constructed for guiding and preparing other bone joints for receiving prosthetic components. Patient-specific guides can be, for example, constructed for the knee, the hip, the shoulder, etc, and can include two or more relatively movable and interconnected components. When more than two components are used, the same or different coupling mechanisms 920 can be provided along the interfaces of the adjacent components. Each of the components can match a corresponding anatomic portion in three dimensions and can be configured for surgical placement on the patient and can include a guiding formation that is related to an axis associated with the anatomic portion. Such axes can tangential or perpendicular or at other specified angle relative to the anatomic portion, such as, for example axes A and B shown in FIG. 19. The axes A and B can have, for example, specified orientations relative to various anatomic axes of the joint, such as the mechanical axis discussed above.

In another aspect, and referring to FIGS. 21-23C, a patient-specific alignment guide 1000 according to the present teachings provides optionally selectable or adjustable features that can accommodate intra-operative decisions or other changes of the surgical plan in the operating room, as discussed below. As discussed above, the alignment guide 1000 can be generally formed using computer modeling for matching a three-dimensional image of the patient's bone surface (with or without the cartilage) by known methods.

Figure 21:
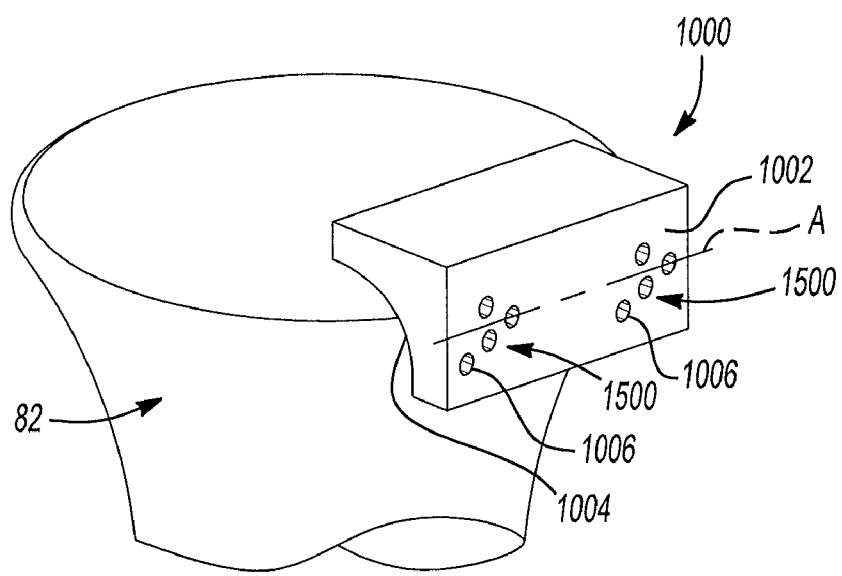
FIG. 21 is a perspective view of an exemplary alignment guide according to the present teachings shown on a joint surface.

Referring to FIG. 21, the alignment guide 1000 includes an inner three-dimensional surface 1004 adapted to closely conform or match a joint surface 82 of the patient. The joint surface 82 can be a bone surface with or without soft tissue, such as articular cartilage for the knee or other joint soft tissue. The alignment guide 1000 can include an outer guiding surface 1002 adapted to receive a drill guide 1030, such as the drill guide 1030 shown in FIG. 21B, or other cutting/reaming/drilling guide instrument. The alignment guide 1000 can include an adjustment mechanism 1500, which can be used to allow deviations from the pre-operative plan during surgery. In the exemplary illustration of FIG. 21, the adjustment mechanism 1500 includes a plurality of pairs of guiding apertures 1006 that are arranged on the outer surface 1002 of the alignment guide 1000 to enable mounting of a drill guide 1030, in a plurality of orientations and/or relative to an axis A of the alignment guide.

Figure 21A:
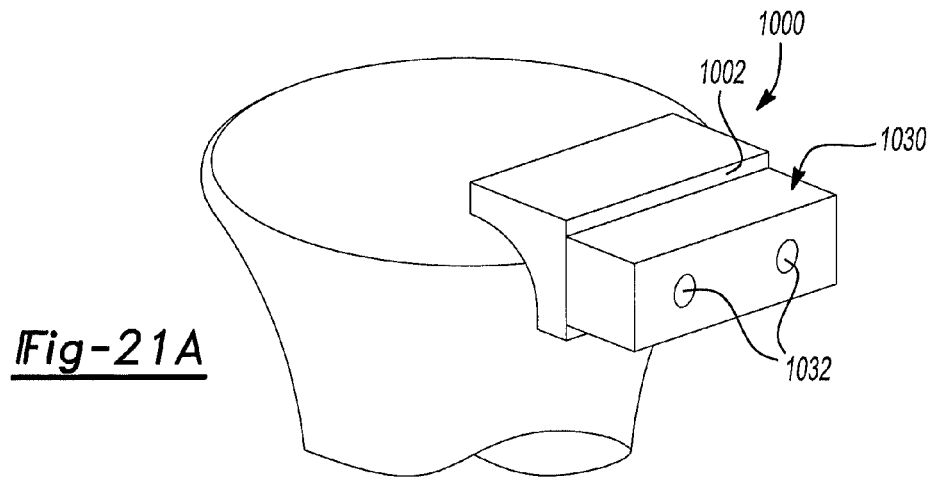
FIG. 21A is an environmental view of an exemplary alignment guide according to the present teachings shown on a joint surface assembled with a drill guide.
Figure 21B:
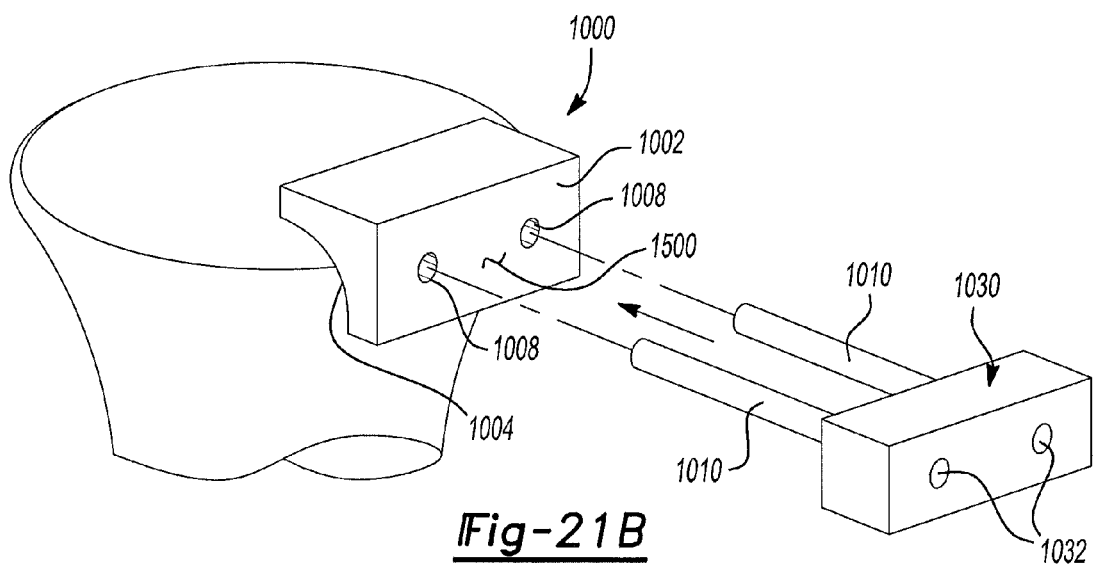
FIG. 21B is an exploded view of the alignment guide and drill guide of FIG. 21A.
Figure 21C:
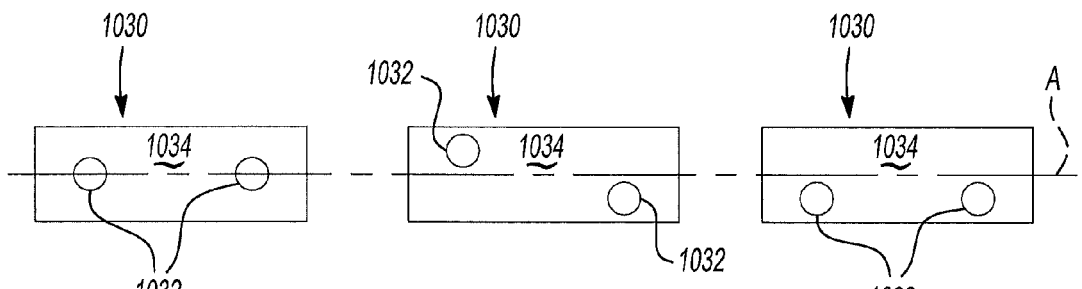
FIG. 21C illustrates three different exemplary arrangements of a drill guide for the alignment guide of FIG. 21A, each shown in side view.

Referring to FIGS. 21A-C, the adjustment mechanism 1500 can be in the form of a single pair of bigger guiding slots or apertures 1008 that are sized and shaped such that a variety of drill guides 1030 with different drill guide geometries can be accommodated. The drill guide 1030 can include, for example, a pair of drill apertures 1032 on a face 1034 of the drill guide 1030 for receiving corresponding guide pins 1010. The pair of drill apertures 1032 can be arranged along a central axis A of the face 1034 of the drill guide 1030 defining a neutral position, or diagonally offset relative to the axis A, or parallel and offset relative to the axis A. It will be appreciated that although three exemplary arrangements are illustrated, the pair of drill apertures 1032 can be orientated at any angle or distance relative to the axis A. Certain orientations and distances can be selected based on the particular arthroplastic procedure and the corresponding anatomic or biomechanical axes.

Referring to FIGS. 22A-23C, exemplary illustrations of an adjustment mechanism 1500 that allows rotation of the drill guide 1030 relative to the alignment guide 1000 are shown. Referring to FIG. 22A, for example, the adjustment mechanism 1500 can be in the form of an interior guiding cavity or aperture 1022 adapted to support a block 1040 on which the drill guide 1030 can be rotationally mounted. The drill guide 1030 can rotate relative to the block 1040 in the directions indicated by double arrow "B". A rotational curved scale 1042 on the block 1040 can indicate the angle of rotation on the rotational plane defined by arrow B. Alternatively, the adjustment mechanism 1500 can be a pivot or hinge connector to the drill guide 1030, as provided, for example, by the combination of the slot 1022 and the block 1040 shown in FIG. 22A.

Referring to FIG. 22B, the adjustment mechanism 1500 allows translational and rotational motion of the drill guide 1030 relative to the alignment guide 1000. For example, the adjustment mechanism 1500 can be configured so that the block 1040 can move in a translation mode relative to the alignment guide 1000 as indicated by arrows "E", in addition to the rotational movement in the direction of the double arrow B. Accordingly, the adjustment mechanism 1500 can be any connector or feature that allows translational or rotational motion of the drill guide 1030 relative to the alignment guide 1000.

Referring to FIGS. 23A-23C, for example the block 1040 supported on the alignment guide 1000 can include a guiding aperture 1046. The drill guide 1030 can be rotationally supported in the guiding aperture 1046 such that it can rotate in two opposite directions as indicated by arrows "C" and "D", as shown in FIGS. 23A and 23B, relative to a neutral position shown in FIG. 23C. It will be appreciated that the rotational motion indicated by arrows C and D is on a plane orthogonal to the motion indicated by arrow B in FIGS. 22A and 22B. The drill guide 1030 can include a scale 1044 indicating the angle of rotation on the plane of rotation defined by arrows C and D. It will be appreciated that the block 1040 can be a modular or integral part of the alignment guide 1000, or a separate component.

The illustrations of the adjustment mechanism 1500 of the alignment guide 1000 are only exemplary. As described above, the adjustment mechanism 1500 can be an arrangement of pairs of guiding apertures, a pair of enlarged guiding apertures, a single guiding aperture, a cavity, a slot, a hinge, a pivot or other feature or connector that allows rotational motion in one or two orthogonal planes and/or translational motion between the alignment guide 1000 and the drill guide 1030.

It will be appreciated that the alignment guide 1000 and drill guide 1030 as described above can be constructed for various joints, including the knee, the hip, the shoulder, etc. The present teachings combine all the features of patient-specific alignment guides 1000 that can be customized and prepared in pre-operative planning and delivered with a surgical plan in time for the surgical operation with the added flexibility of accommodating intra-operative or other last minute changes to surgical plan in the operating room by using the provided adjustment mechanism to change the orientation and location of the drill guides relative the patient specific alignment guide.

Figure 24:
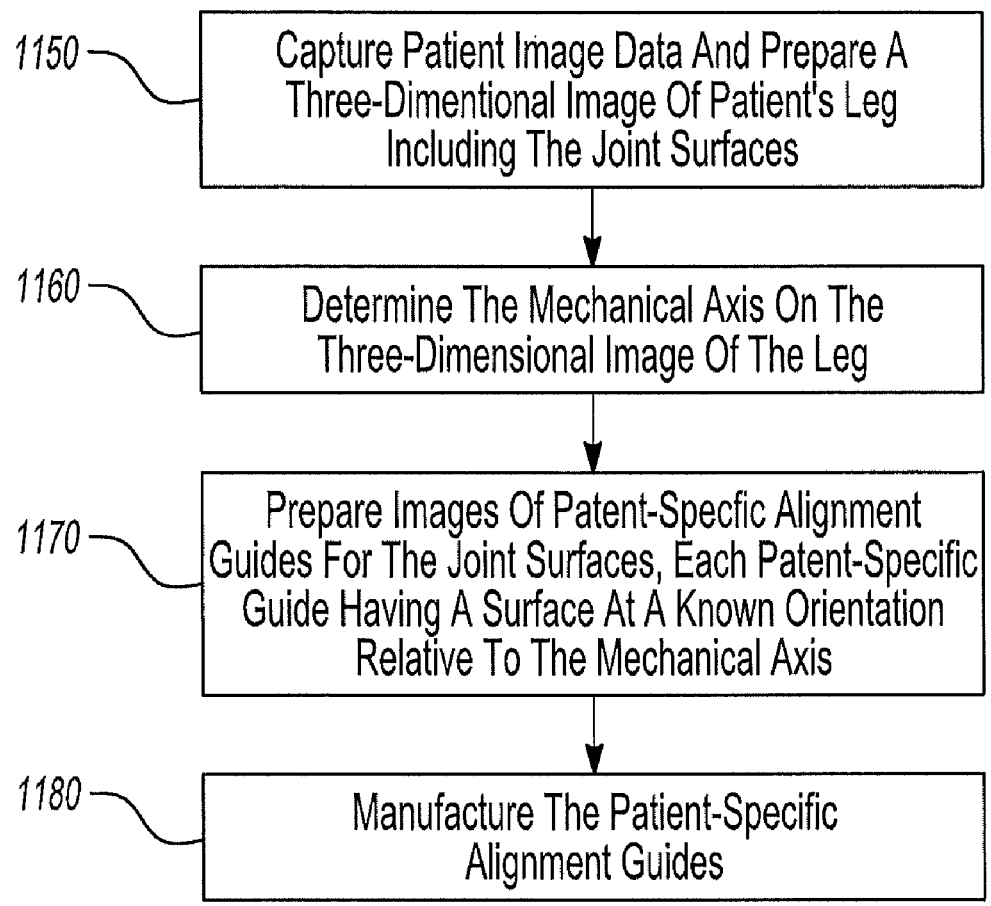
FIG. 24 illustrates a method for preparing patient-specific alignment guides.

According to the present teachings, and as discussed above, patient-specific alignment guides can be manufactured based on pre-operative designs developed in conjunction with pre-operative alignment techniques. The alignment techniques include determination of the mechanical axis and possibly other anatomic axes in three-dimensional imaging of the leg, as discussed above in reference to FIGS. 2-4. For example, and referring to FIG. 24, during pre-operative planning, patient image data can be captured by MRI or CT scans and a three-dimensional image of the patient's leg including the joint surfaces can be prepared, at 1150. The mechanical axis of the leg can be determined on the three-dimensional image of the leg, at 1160. It will be appreciated that other axes related to the leg or joint can be also determined on the same three-dimensional image, such as, for example various anatomic axes. Images of patient-specific alignment guides for the joint surfaces can be designed such that the alignment guides reference the mechanical axis, at 1170. The alignment guides, for example, can have a guide surface that is at known orientation to the mechanical axis when the alignment guide's patient engaging surface is fitted on the joint surface, as discussed below. Consequently, the alignment guides, when engaging the corresponding surface of the joint of the patient for whom the guides were designed, are already automatically referencing the mechanical axis and there is no need to determine the center of the femoral head or the mechanical axis intra-operatively. The physical alignment guides can then be manufactured from the image data by rapid prototyping, machining or other methods, at 1180.

Referring to FIGS. 24-28, any balancing method that requires the use of a balancing tensor device to balance the tension of the soft tissue associated with the joint can omit the time-consuming and often inaccurate procedure of determining the center of the femoral head. Rather, the soft-tissue can be balanced relative to the alignment guide, which is already referencing the mechanical axis of the patient's joint.

Figure 25:
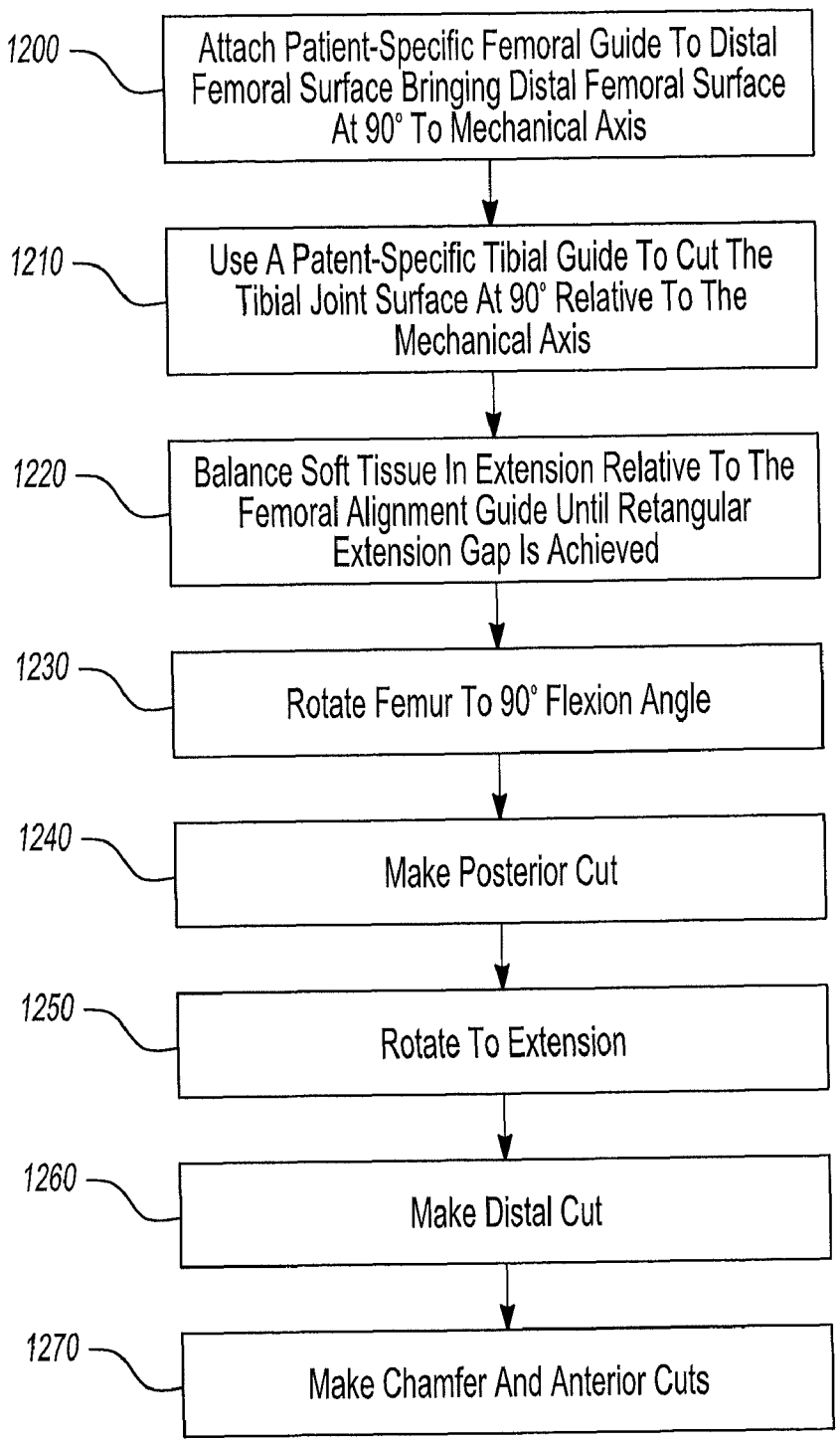
FIG. 25 illustrates a method for balancing soft tissue in knee surgery.
Figure 26:
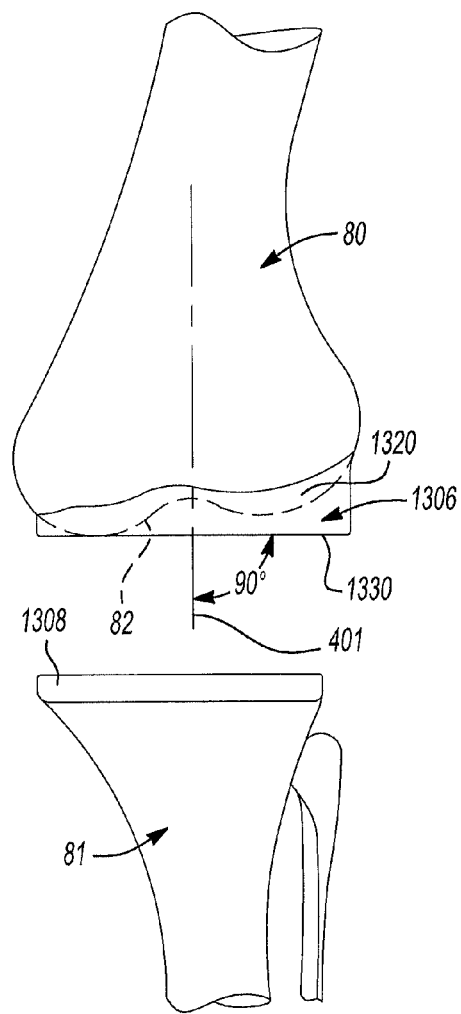
FIG. 26 is an environmental view of patient-specific alignment guides according to the present teachings.

Referring to FIGS. 25 and 26, an exemplary balancing procedure can include the following aspects. A patient-specific femoral alignment guide 1306 can include a femoral three-dimensional nesting surface 1320 conforming in nesting relationship with the distal femoral surface 82 of the distal femur 80 and a tibia-facing guide surface 1330 oriented at a 90-degree or other desired angle relative to the mechanical axis 401. The patient-specific femoral alignment guide 1306 can be attached to the distal femoral surface 82 at 1200, thereby aligning the distal femoral surface 82 relative to the mechanical axis 401, at a 90-degree or other desired angle. The femoral alignment guide 1306 can only be placed uniquely in a nesting, form-fitting position on the distal femoral surface 82, such that upon engagement, the distal femoral surface 82 and the guide surface 1330 are oriented at a 90-degree angle relative to the mechanical axis 401, as determined in the pre-operative plan on which the design of the femoral alignment guide 1306 was based. Similarly, a patient-specific tibial alignment guide 1308 can be attached to the proximal tibia 81 in a unique position at a 90-degree angle relative to the mechanical axis 401. Alternatively, the patient-specific tibial alignment guide 1308 can be used to cut the tibia at a 90-degree angle relative to the mechanical axis 401, at 1210.

The balancing procedure can then proceed without the need to determine the head of the femur, as the mechanical axis is already referenced correctly by the femoral alignment guide 1306. The associated soft tissues can be balanced in extension relative to the guide surface 1330 of the femoral alignment guide 1306, rather than to the mechanical axis 401, until a rectangular extension gap is achieved, at 1220. A balancing tensor 1400 can be used for soft tissue balancing, as discussed below. The femur 80 can be rotated to a 90-degree flexion angle, at 1230, and a posterior cut can be made at 1240. The femur 80 can be rotated back to extension at 1250, and a distal cut can be made at 1260. The chamfer and anterior cuts can be made at 1270.

Figure 27:
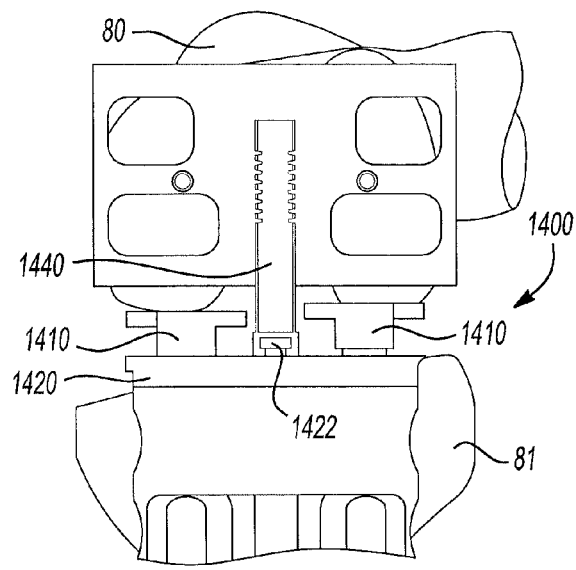
FIG. 27 is an environmental view of a balancing tensor shown in flexion.
Figure 28:
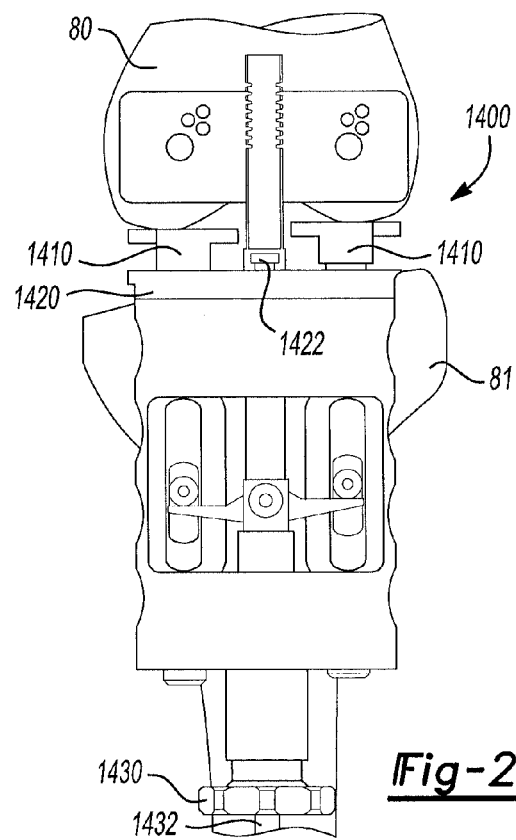
FIG. 28 is an environmental view of the balancing tensor of FIG. 27 shown in extension.

An exemplary, known in the art, balancing knee tensor 1400 is illustrated in FIGS. 27 and 28 in flexion and extension, respectively, although other tensors can also be used. The tensor 1400 can include first and second femoral paddles 1410, a tibial sled 1420 having a T-rail 1422, a calibrated slide 1440, and a knob 1430 with a scale 1432 for controlling tension. The tibial sled 1420 can be placed on the tibial alignment guide 1308, shown in FIG. 26, and the femoral paddles 1410 can be placed under the femoral alignment guide 1306, shown in FIG. 26. Balancing can be performed by applying appropriate tension in flexion and extension by rotating the knob 1430. The sizes of flexion and extension gaps can be read on the calibrated slide 1440 and should be substantially equal.

As discussed above, the present teachings eliminate the need to determine the center of the femoral head intra-operatively, or to determine the mechanical axis, or to balance the soft tissues relative to the mechanical axis. Soft tissue balancing can be performed relative to the femoral alignment guide 1306, which is already aligned relative to the mechanical axis 401 when placed on the distal femur 80. Accordingly, the present teachings can reduce intra-operative time and simplify soft tissue balancing by eliminating the time-consuming, difficult and possibly inaccurate process of intra-operatively determining the center of the head of the femur.

Figure 29:
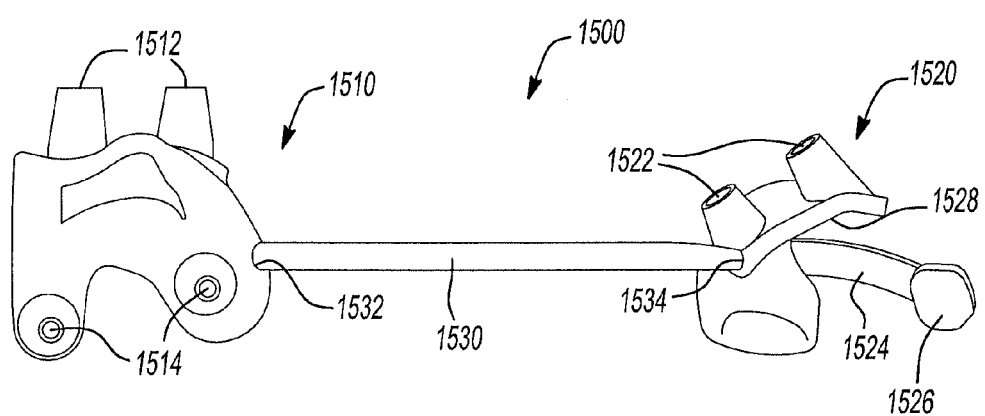
FIG. 29 is a perspective view of an assemblage of interconnected patient-specific alignment guides.

Referring to FIG. 29, an exemplary patient-specific assemblage 1500 can be provided to connect multiple patient-specific alignment guides 1510, 1520 and/or other patient-associated components during the manufacture and delivery of the components. The assemblage 1500 can ensure that associated components stay together and are not misplaced or mixed up. In the illustrative example of FIG. 29, the assemblage 1500 includes a connection arm 1530 coupled to a femoral alignment guide 1510 at a first connection end 1532 and to a tibial alignment guide 1520 at a second connection end 1534. The first and second connection ends 1532, 1534 can have undercuts or other built-in weakening or frangible features, so that the connection arm 1530 can be broken off before use to separate the alignment guides 1510, 1520 from each other. In another aspect, the frangible features can be placed in additional or other locations intermediate the first and second ends. The connection arm 1530 can be a monolithic bar, which can be either substantially rigid or a flexible. In other aspects, the connection arm 1530 can include multiple interconnected linkages, and can also be a chain having multiple links, allowing disconnection at any link.

As illustrated in FIG. 29, the femoral alignment guide 1510 can include various guiding portions 1512, 1514 for inserting drills, or other instruments, and fixation fasteners or pins. The tibial alignment guide 1520 can also include guiding portions 1522, and a stabilizer arm 1524 having a plate 1526 for engaging the lateral surface of the tibia when the underside 1528 of the tibial alignment guide 1520 engages the tibial plateau. The connection arm 1530 can hold the associated parts together to prevent their disassociation or misplacement during delivery. In one aspect, the connection arm 1530 can hold the associated parts in a spaced apart relationship at some distance relative to each other, such that rubbing between the parts and resulting deformation or breakage can be avoided. Further, the connection arm 1530 can be held such that the alignment guides 1510, 1520 are suspended and immovable. The connection arm can be made from various material including materials used for constructing the alignment guides or other materials including nitinol, for example. Although two alignment guides are shown coupled to the connection arm 1530, it will be appreciated that additional guides or other components can be similarly connected in one assemblage using with one or more connection arms.

The foregoing discussion discloses and describes merely exemplary arrangements of the present teachings. One skilled in the art will readily recognize from such discussion, and from the accompanying drawings, that various changes, modifications and variations can be made therein without departing from the spirit and scope of the present teachings.

What is claimed is:

1. An orthopedic apparatus comprising:
a multi-component patient-specific alignment guide attachable to a surface of a proximal femoral bone of a patient receiving a prosthetic implant, the guide comprising at least first and second components adjacent to one another, the first component having a first three-dimensional bone engagement surface and the second component having a second three-dimensional bone engagement surface, the first and second bone engagement surfaces configured preoperatively from three-dimensional images of the bone of the patient from imaging scans of the patient to anatomically match corresponding first and second portions of the surface of the bone, and wherein the first component has a head portion configured to engage and anatomically match a corresponding portion of a femoral head of the femoral bone and a first neck portion configured to engage and anatomically match a corresponding portion of a femoral neck of the patient, and wherein the second component has a second neck portion configured to engage and match a remaining portion of the femoral neck of the patient, wherein the first neck and second portions are configured to surround completely the entire femoral neck of the patient;
at least one alignment formation for guiding a drill and formed in the first component and passing perpendicularly through the head portion of the first component; and
a coupling mechanism removably connecting the first and second components to one another such that the patient-specific guide can be positioned to completely surround and contact the entire femoral neck of the patient.

2. The orthopedic apparatus of claim 1, wherein the alignment formation defines a guiding bore.

3. The orthopedic apparatus of claim 1, wherein the coupling mechanism is a snap-fit or interlocking mechanism allowing complete separation of the first and second components.

4. The orthopedic apparatus of claim 1, wherein the coupling mechanism is a hinge allowing relative rotation between the first and second components.

5. An orthopedic apparatus comprising:
a patient-specific femoral alignment guide for a knee joint of a patient including:
a first component having a first three dimensional surface conforming in shape to a first portion of a distal femoral surface from a three-dimensional image of the patient's distal femur obtained from preoperative imaging scans of the patient, the first component having an alignment formation referencing a first axis, wherein the first component is configured to engage and anatomically match an osteophyte on the distal femoral surface of the patient; and a second component removably attached to the first component, the second component having a second three-dimensional surface conforming in shape to a second portion of the distal femoral surface of the patient from the three-dimensional image of the patient's distal, the second component having an alignment formation referencing a second axis.

6. The orthopedic apparatus of claim 5, wherein at least one of the first and second components includes an indicator feature associated with a corresponding landmark anatomic feature for guiding placement of the corresponding component.

7. The orthopedic apparatus of claim 6, wherein the indicator feature is a pointing protrusion extending from the corresponding component.

8. A manufacturing assemblage for orthopedic surgery comprising:

a first patient-specific alignment guide configured preoperatively from three-dimensional images of a first joint surface of a patient from imaging scans of the patient to anatomically match the first joint surface of the patient;

a second patient-specific alignment guide configured preoperatively from three-dimensional images of a second joint surface of a patient from imaging scans of the patient to anatomically match the second joint surface of the patient; and a frangible connection arm coupled to the first alignment guide at a first connection end and to the second alignment guide at a second connection end, the connection arm configured to retain and associate the first and second patient-specific alignment guides to one another during delivery for surgical use, the connection arm including frangible features configured to break off the connection arm and separate the first and second patient-specific alignment guides for surgical use.

9. The manufacturing assemblage of claim 8, wherein the connection arm includes a plurality of interconnected links.

10. The manufacturing assemblage of claim 8, wherein the frangible features are located adjacent the first and second connection ends.

11. The manufacturing assemblage of claim 8, wherein the first patient-specific alignment guide is a patient-specific femoral alignment guide and the second patient-specific alignment guide is a patient-specific tibial alignment guide for a knee joint of the patient.

12. The orthopedic apparatus of claim 5, wherein the first and second components are rotatable relative to one another.

13. The orthopedic apparatus of claim 5, wherein the first and second components are interlockable.

* * * * *

UNITED STATES PATENT AND TRADEMARK OFFICE
CERTIFICATE OF CORRECTION

PATENT NO. : 8,282,646 B2  
APPLICATION NO. : 12/039849  
DATED : October 9, 2012  
INVENTOR(S) : Ryan J. Schoenefeld et al.

It is certified that error appears in the above-identified patent and that said Letters Patent is hereby corrected as shown below:

In the Specifications:

Column 2, line 63, "view" should be --views--.

Column 3, line 1, "view" should be --views--.

Column 3, line 9, after "is" insert --a--.

Column 3, line 17, "illustrated" should be --illustrates--.

Column 3, line 28, after "FIG. 15B" insert --is--.

Column 3, line 64, "FIG. 3B" should be --FIG. 23B--.

Column 7, line 42, before "associated" insert --be--.

Column 9, line 52, "include" should be --includes--.

Column 10, line 28, after "can" insert --be--.

Column 13, line 51, after "or" delete "a".

Column 14, line 9, "using" should be --used--.

In the Claims:

Column 15, line 8, Claim 5, after "distal" insert --femur--.

Signed and Sealed this  
Third Day of September, 2013

Teresa Stanek Rea  
*Acting Director of the United States Patent and Trademark Office*